(12) United States Patent
Brannan et al.

(10) Patent No.: US 8,287,527 B2
(45) Date of Patent: Oct. 16, 2012

(54) MICROWAVE SYSTEM CALIBRATION APPARATUS AND METHOD OF USE

(75) Inventors: Joseph D. Brannan, Erie, CO (US); Joseph A. Paulus, Louisville, CO (US)

(73) Assignee: Vivant Medical, Inc., Boulder, CO (US)

( * ) Notice: Subject to any disclaimer, the term of this patent is extended or adjusted under 35 U.S.C. 154(b) by 1051 days.

(21) Appl. No.: 12/241,983

(22) Filed: Sep. 30, 2008

(65) Prior Publication Data
US 2010/0082084 A1    Apr. 1, 2010

(51) Int. Cl.
*A61B 18/18* (2006.01)
(52) U.S. Cl. .......... 606/33; 607/101
(58) Field of Classification Search .......... 606/33; 607/100, 102, 103, 115
See application file for complete search history.

(56) References Cited

U.S. PATENT DOCUMENTS

| | | |
|---|---|---|
| 3,998,538 A | 12/1976 | Urso |
| 4,204,549 A | 5/1980 | Paglione |
| 4,228,809 A | 10/1980 | Paglione |
| 4,247,815 A | 1/1981 | Larsen |
| 4,311,154 A | 1/1982 | Sterzer et al. |
| 4,741,348 A | 5/1988 | Kikuchi |
| 4,744,372 A | 5/1988 | Kikuchi |
| 5,097,846 A | 3/1992 | Larsen |
| 5,354,325 A | 10/1994 | Chive |
| 5,364,392 A | 11/1994 | Warner |
| 5,405,346 A | 4/1995 | Grundy et al. |
| 5,562,720 A | 10/1996 | Stern et al. |
| 5,651,780 A | 7/1997 | Jackson |
| 5,683,382 A | 11/1997 | Lenihan et al. |
| 5,865,788 A | 2/1999 | Edwards et al. |
| 5,904,709 A | 5/1999 | Arndt et al. |
| 5,931,836 A | 8/1999 | Hatta et al. |
| 5,957,969 A | 9/1999 | Warner et al. |
| 5,961,871 A | 10/1999 | Bible et al. |
| 5,983,141 A | 11/1999 | Sluijter et al. |
| 6,016,452 A | 1/2000 | Kasevich |
| 6,067,475 A | 5/2000 | Graves et al. |
| 6,097,985 A | 8/2000 | Kasevich et al. |
| 6,134,476 A | 10/2000 | Arndt et al. |
| 6,165,173 A | 12/2000 | Kamdar |
| 6,175,768 B1 | 1/2001 | Arndt et al. |
| 6,181,970 B1 | 1/2001 | Kasevich |
| 6,216,704 B1 | 4/2001 | Ingle et al. |
| 6,233,490 B1 | 5/2001 | Kasevich |
| 6,246,912 B1 | 6/2001 | Sluijter et al. |
| 6,273,886 B1 | 8/2001 | Edwards et al. |
| 6,358,245 B1 | 3/2002 | Edwards et al. |
| 6,471,696 B1 | 10/2002 | Berube et al. |

(Continued)

FOREIGN PATENT DOCUMENTS
DE        179607        3/1905
(Continued)

OTHER PUBLICATIONS

International Search Report EP09012392 dated Mar. 30, 2010.
(Continued)

*Primary Examiner* — Michael Peffley
*Assistant Examiner* — Thomas Giuliani

(57) ABSTRACT

An apparatus for calibrating a microwave energy delivery device including a body, the body defining a chamber portion. The chamber portion is configured to receive a portion of a microwave energy delivery device and the body is configured to absorb energy transmitted by the microwave energy delivery device at a predetermined absorption rate.

14 Claims, 11 Drawing Sheets

U.S. PATENT DOCUMENTS

| | | |
|---|---|---|
| 6,485,486 B1 | 11/2002 | Trembly et al. |
| 6,699,241 B2 | 3/2004 | Rappaport et al. |
| 6,743,225 B2 | 6/2004 | Sanchez et al. |
| 6,784,405 B2 | 8/2004 | Flugstad et al. |
| 6,847,848 B2 | 1/2005 | Sterzer et al. |
| 7,226,446 B1 | 6/2007 | Mody et al. |
| 7,344,533 B2 | 3/2008 | Pearson et al. |
| 7,393,352 B2 | 7/2008 | Berube |
| 7,419,487 B2 | 9/2008 | Johnson et al. |
| 2002/0087151 A1 | 7/2002 | Mody et al. |
| 2003/0153908 A1 | 8/2003 | Goble et al. |
| 2004/0133189 A1 | 7/2004 | Sakurai |
| 2004/0243120 A1 | 12/2004 | Orszulak |
| 2005/0033278 A1 | 2/2005 | McClurken et al. |
| 2006/0055591 A1 | 3/2006 | Eriksson |
| 2006/0079774 A1 | 4/2006 | Anderson |
| 2006/0155270 A1 | 7/2006 | Hancock et al. |
| 2006/0224152 A1 | 10/2006 | Behnke et al. |
| 2007/0203480 A1 | 8/2007 | Mody et al. |
| 2007/0233057 A1 | 10/2007 | Konishi |
| 2007/0282319 A1 | 12/2007 | Van Der Weide et al. |
| 2009/0018536 A1 | 1/2009 | Behnke |
| 2010/0082085 A1 | 4/2010 | Pai et al. |
| 2010/0168730 A1 | 7/2010 | Hancock et al. |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 0296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 1186274 | 4/2006 |
| EP | 880220 | 6/2006 |
| EP | 1810630 | 7/2007 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 2164473 | 3/1986 |
| GB | 2214430 | 9/1989 |
| GB | 2358934 | 8/2001 |
| GB | 2434872 | 8/2007 |
| SU | 166452 | 1/1965 |
| SU | 727201 | 4/1980 |
| WO | WO 9207622 | 5/1992 |
| WO | WO 2004047659 | 6/2004 |
| WO | WO2005115235 | 12/2005 |
| WO | WO2006/105121 | 10/2006 |
| WO | WO2007055491 | 5/2007 |
| WO | WO 2007055491 | 5/2007 |
| WO | WO 2007105963 | 9/2007 |
| WO | WO2008/043999 | 4/2008 |
| WO | WO2008043999 | 4/2008 |
| WO | WO2008044000 | 4/2008 |
| WO | WO 2008044013 | 4/2008 |
| WO | WO2008044013 | 4/2008 |
| WO | WO 2008071914 | 6/2008 |
| WO | WO2008/110756 | 9/2008 |
| WO | WO 2008110756 | 9/2008 |

OTHER PUBLICATIONS

International Search Report EP09012386 dated Apr. 1, 2010.
International Search Report EP09012396 dated Apr. 7, 2010.
International Search Report EP09012400 dated Apr. 7, 2010.
International Search Report EP 09012388.6 dated Apr. 13, 2010.
International Search Report EP 09012391.0 dated Apr. 19, 2010.
International Search Report EP 09012389 dated Jun. 7, 2010.
U.S. Appl. No. 12/057,557, filed Mar. 28, 2008.
U.S. Appl. No. 10/406,690, filed Apr. 3, 2003.
U.S. Appl. No. 11/242,458, filed Oct. 3, 2005.
U.S. Appl. No. 10/573,713, filed Mar. 28, 2006.
U.S. Appl. No. 12/136,620, filed Jun. 10, 2008.
U.S. Appl. No. 12/389,168, filed Feb. 19, 2009.
U.S. Appl. No. 12/351,935, filed Jan. 12, 2009.
U.S. Appl. No. 12/401,981, filed Mar. 11, 2009.
U.S. Appl. No. 12/351,947, filed Jan. 12, 2009.
U.S. Appl. No. 12/407,896, filed Mar. 20, 2009.
U.S. Appl. No. 12/205,525, filed Sep. 5, 2008.
U.S. Appl. No. 12/249,263, filed Oct. 10, 2008.
U.S. Appl. No. 12/249,218, filed Oct. 10, 2008.
U.S. Appl. No. 12/351,970, filed Jan. 12, 2009.
U.S. Appl. No. 12/351,960, filed Jan. 12, 2009.
U.S. Appl. No. 12/205,298, filed Sep. 5, 2008.
U.S. Appl. No. 12/351,980, filed Jan. 12, 2009.
U.S. Appl. No. 12/203,734, filed Sep. 3, 2008.
U.S. Appl. No. 12/242,102, filed Sep. 30, 2008.
U.S. Appl. No. 12/241,861, filed Sep. 30, 2008.
U.S. Appl. No. 12/242,061, filed Sep. 30, 2008.
U.S. Appl. No. 12/242,026, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.

Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.

Geddes et al., "The Measurement of Physiologic Events by Electrical Impedance" Am. J. MI, Jan. Mar. 1964, pp. 16-27.

Cosman et al., "Methods of Making Nervous System Lesions" in William RH, Rengachary SS (eds): Neurosurgery, New York: McGraw-Hill, vol. 111, (1984), pp. 2490-2499.

Anderson et al., "A Numerical Study of Rapid Heating for High Temperature Radio Frequency Hyperthermia" International Journal of Bio-Medical Computing, 35 (1994) pp. 297-307.

Cosman et al., "Radiofrequency Lesion Generation and Its Effect on Tissue Impedance" Applied Neurophysiology 51: (1988) pp. 230-242.

Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

International Search Report EP 98300964.8 dated Dec. 4, 2000.
International Search Report EP 04009964 dated Jul. 13, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 5, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated.Dec. 1, 2008.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.

MICROWAVE SYSTEM CALIBRATION APPARATUS AND METHOD OF USE

BACKGROUND

1. Technical Field

The present invention relates to systems and methods for performing a medical procedure, wherein the medical procedure includes the generation and transfer of energy from an energy source to a dynamically changing device and, more particularly, efficient transfer of energy through a microwave energy delivery, measurement and control system.

2. Description of Related Art

During microwave ablation procedures, the electrical performance of a microwave antenna probe changes throughout the course of an ablation treatment. The change in performance may be due to the device or due to changes in tissue properties. The ability to observe parameters indicative of changes in antenna property, antenna performance or tissue properties changes during ablation greatly aids in the understanding of microwave ablation.

For example, measuring antenna impedance is a common method for determining antenna performance and/or a change in an antenna property. Microwave systems are typically designed to a characteristic impedance, such as, for example, 50 Ohms, wherein the impedance of the generator, the delivery system, the ablation device and tissue are about equal to the characteristic impedance. Efficiency of energy delivery decreases when the impedance of any portion of the system changes.

With low frequency RF systems impedance can easily be determined by measuring the delivered current at a known voltage and calculating tissue impedance using well known algorithms. Obtaining accurate measurements of tissue impedance at microwave frequencies is more difficult because circuits behave differently at microwave frequency. For example, unlike an electrode in an RF system, an antenna in a microwave system does not conduct current to tissue. In addition, other components in a microwave system may transmit or radiate energy, like an antenna, or components may reflect energy back into the generator. As such, it is difficult to determine what percentage of the energy generated by the microwave generator is actually delivered to tissue, and conventional algorithms for tissue impedance are inaccurate.

Therefore, other methods of measuring impedance are typically used in a microwave system. One well known method is an indirect method using measurements of forward and reflected power. While this is a generally accepted method, this method can also prove to be inaccurate because the method fails to account component losses and depends on indirect measurements, such as, for example forward and reflected power measurements from directional couplers, to calculate impedance. In addition, this method does not provide information related to phase, a component vital to determining antenna impedance.

One alternative method of measuring impedance in a microwave energy delivery system is by determining broadband scattering parameters. Capturing antenna broadband scattering parameters periodically throughout a high power ablation cycle necessitates the use of equipment that requires precise calibration. Unfortunately, this equipment is prone to damage by high power signals and the microwave energy delivery system typically needs to be reconfigured to accommodate and protect such equipment.

The present disclosure describes a Microwave Research Tool (MRT) that includes a system to measure impedance in a microwave energy delivery system by direct and indirect methods including a system to measure broadband scattering parameters.

SUMMARY

The present disclosure relates to an apparatus for calibrating a microwave energy delivery device including a body defining a chamber portion therein, the chamber portion configured to receive a portion of a microwave energy delivery device and the body is configured to absorb energy transmitted by the microwave energy delivery device at a predetermined absorption rate.

The chamber partially surrounds the microwave antenna of the microwave energy delivery device. The chamber is formed by the body is an elongate cylindrical chamber, the elongate cylindrical chamber adapted to receive the microwave antenna of the microwave energy delivery device.

In another embodiment the chamber is configured to engage the microwave antenna of the microwave energy delivery device within the chamber.

The body further includes a first body portion configured to receive and position the microwave energy delivery device and a second body portion configured to engage the first body portion and form the chamber therebetween. The first body portion and the second body portion may be hingedly engaged. The first and second body portions may include a locking mechanism that locks the calibration device to the microwave energy delivery device. The locking mechanism may be a clip, a latch, a pin, a locking hinge, a self closing hinge, a magnetic lock or an electronic closure mechanism.

In yet another embodiment the body may includes a positioner to position the microwave energy delivery device in a fixed position relative to the chamber. The positioner on the body may correspond to a substantially similar interface on the microwave energy device. The positioner and the interface may mate with each other to position the microwave energy delivery device in a fixed position relative to the chamber. The positioner may be recessed portion of the body and the interface may be a raised portion of the microwave energy delivery device. The recessed portion and the raised portion mate together and position the microwave energy delivery device.

The first body portion and the second body portion surround a portion of the microwave energy delivery device in a first condition and are spaced relative to a portion of the microwave energy delivery device in a second condition.

A system for calibrating a microwave energy delivery device is also disclosed and includes a microwave generator configured to deliver a microwave energy signal to a microwave energy delivery device and a microwave system calibration apparatus. The microwave system calibration apparatus includes a body defining a chamber portion therein, the chamber portion configured to receive a portion of the microwave energy delivery device. The body configured to absorb microwave energy transmitted by the microwave energy delivery device at a predetermined absorption rate. The microwave generator measures a measured parameter related to the microwave energy signal delivered to the microwave energy delivery device and determines at least one calibration parameter related to the calibration of the microwave energy delivery device.

The chamber in the system may partially surround the microwave antenna of the microwave energy delivery device. The chamber, formed by the body, may be an elongate cylindrical chamber adapted to receive the microwave antenna of the microwave energy delivery device. The chamber may engage the microwave antenna of the microwave energy delivery device within the chamber.

The measured parameter may be forward power, reflected power or temperature and the calibration parameter may be phase, frequency or impedance.

In another embodiment of the system the microwave generator may determine engagement of the microwave energy delivery device with the microwave system calibration apparatus.

A method of calibrating a microwave energy delivery system is also disclosed and includes the steps of: connecting a microwave energy delivery device to a microwave generator; positioning the microwave energy delivery device in a chamber defined in a microwave energy calibration apparatus; delivering microwave energy to the microwave energy delivery device; measuring at least one measured parameter related to the energy delivery; determining at least one calibration parameter related to the calibration of the microwave energy device and utilizing the calibration parameter in a subsequent energy delivery.

DETAILED DESCRIPTION

Detailed embodiments of the present disclosure are described herein; however, it is to be understood that the disclosed embodiments are merely exemplary and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 1:
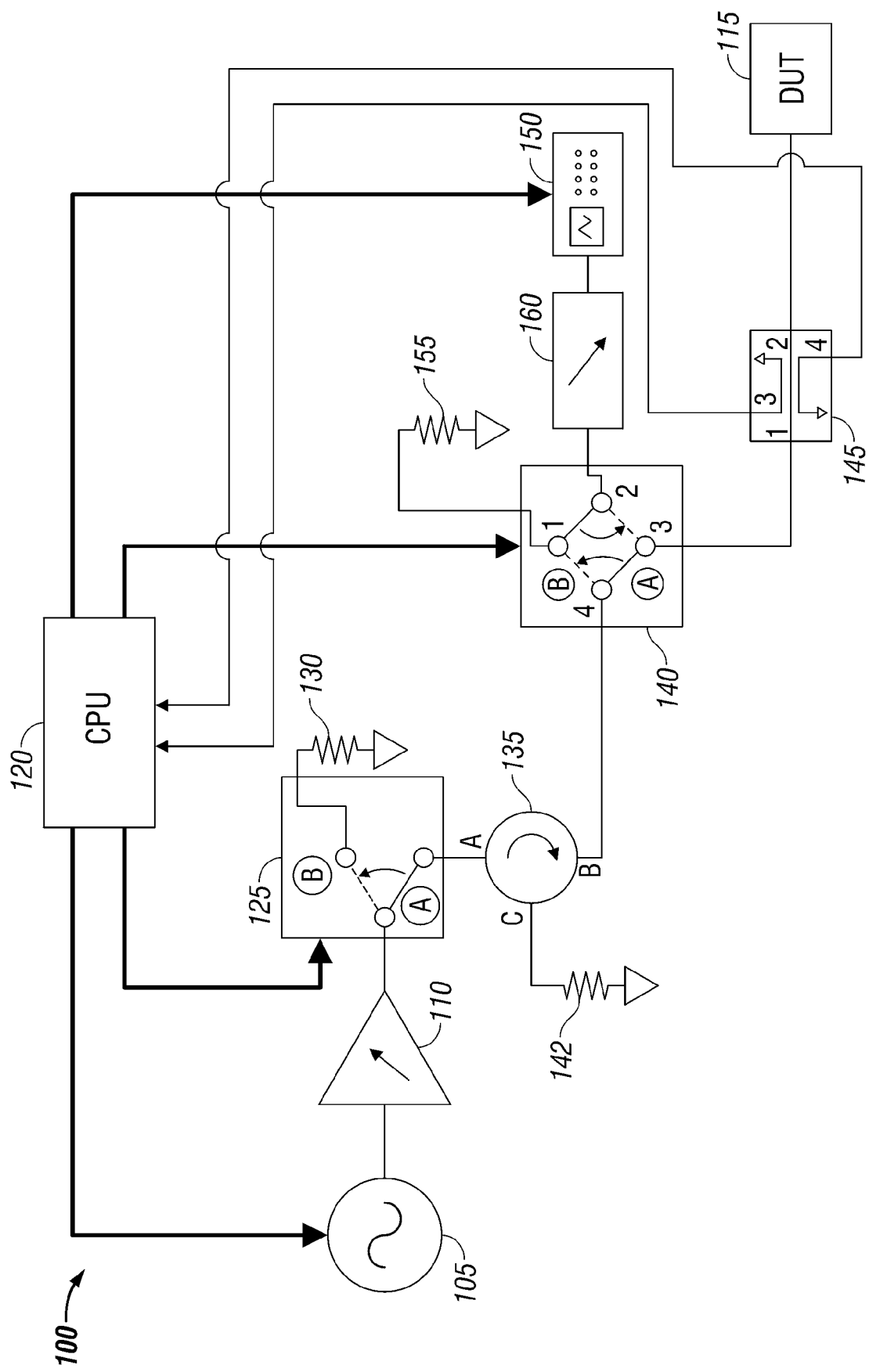
FIG. 1 is a functional block diagram of a microwave energy delivery, measurement and control system in an energy delivery mode according to an embodiment of the present disclosure.

Referring to FIG. 1, a Microwave Research Tool (MRT) including a measurement and control system for use in performing a medical procedure or medical procedure testing, employing embodiments of the present disclosure is generally designated 100. MRT 100 may provide all the functionality of a microwave generator typically used to deliver microwave energy in a medical procedure but with improved functionality as described herewithin. MRT 100 includes individual components, as illustrated in FIG. 1, or the functionality of individual components may be combined or included in one or more components. Components are interconnected with suitable cables and/or connectors.

MRT 100 includes a microwave energy delivery system, a measurement system and a supervisory control system. Each system is described individually although each system may share common components as discussed hereinbelow.

The microwave energy delivery system includes a signal generator 105 capable of generating and supplying a high frequency microwave signal to an amplifier 110. Signal generator 105 may be a single frequency generator or may include variable frequency capability. Signal generator 105 may also be capable of providing a signal including two or more frequencies wherein the device under test 115 (DUT) resonates at two or more frequencies. Supervisory control system may control various aspects of the signal generator 105 such as, for example, the signal delivery timing, the frequency (or frequencies) of the output and the phase of the signal.

Amplifier 110 receives and amplifies the signal from the signal generator 105 to a desirable energy level. Amplifier 110 may be a single or multi-stage amplifier 110 and may include one or more signal conditioning circuits or filters (not shown) such as, for example, a low, high or bandpass circuits. Amplifier 110 gain may be fixed or controlled by a suitable controller, such as, for example, a control algorithm in the supervisory control system, a central processing unit 120 (CPU) or by manual adjustment (not shown).

Amplifier 110 supplies a continuous, amplified microwave signal to a hot switch relay 125. Hot switch relay 125 is controlled by the supervisory control system or CPU 120 and switches the amplified microwave signal to one of an amplifier burn-off load resistor 130 and a circulator 135. The hot switch relay 125 in Position A delivers energy to the DUT 115 through the circulator 135. The hot switch relay 125 in Position B delivers energy away from the DUT 115 and into an amplifier burn-off load resistor 130.

Hot switch relay 125 may be any suitable solid-state high power switch capable of switching a high power microwave energy signal. Hot switch relay 125 receives the high power microwave signal from the signal generator 105 and amplifier 110, and passes the signal between the amplifier burn-off load resistor 130 or the circulator 135 without powering down the signal generator 105 or amplifier 110. One suitable device is a JFW 50S-1552-N, which is a 150 watt 915 MHz dual pole single-throw solid-state switch that can be powered by two DC supply lines and controlled with a single TTL signal line from a supervisory control system or CPU 120. In use, the JFW 50S-1552-N allows the MRT 100 to provide near instantaneous power (i.e. can provide nearly continuous power with very rapid on/off capabilities) without creating amplifier transients, by eliminating the need to power down the signal generator 105 or amplifier 110.

At times, the MRT may provide two sources of electrical isolation between the microwave energy signal and the measurement devices. For example, the first source of electrical isolation may be provided by the electrical isolation in the hot switch relay 125 between the output of Position A and the output of Position B. This electrical isolation prevents unacceptable amounts of energy from the high power microwave energy signal from being passed to the Position A output and to the measurement system connected thereto. For example, at 915 MHz the JFW 50S-1552-N switch (discussed above) provides about 45 dB of electrical isolation between outputs. The second source of electrical isolation is provided by the transfer switch 140 and the electrical isolation between Port 4 and Port 2 of the transfer switch 140 discussed hereinbelow.

Continuous operation of the signal generator 105 and amplifier 110 prevents the introduction of amplifier 110 transients into the microwave energy delivery system. To maintain continuous operation, the switching time between Positions A and B on the hot switch relay 125 should be sufficiently fast to allow continuous operation of the signal generator 105 and amplifier 110. For example, at 915 MHz the JFW 50S-1552-N switches between Position A and B in about 360 ns and between Positions B and A in about 370 ns.

Amplifier burn-off load resistor 130 may be any suitable coaxial terminator capable of dissipating microwave energy while generating a minimal amount of VSWR, or reflective energy, over the bandwidth of the signal generator 105. One such device is a 1433-3 50-ohm 250-watt coaxial terminator sold by Aeroflex/Weinschel and intended for operation over the bandwidth of DC to 5 GHz. Over the entire bandwidth of the 1433-3 the VSWR is less than 1.1.

Circulator 135 is a passive three port device that eliminates standing waves between the hot switch relay 125 and the transfer switch 140. Circulator 135 passes signals received on Port A to Port B, signals received on Port B to Port C and signals received on Port C to Port A. When hot switch relay 125 is in Position A, the microwave energy signal is passed from Port A of the circulator 135 to the transfer switch 140 connected to Port B. Reflected energy from the transfer switch 140 or the DUT 115, received on Port B, is passed to Port C and dissipated through the reflected energy burn-off load resistor 142. Reflected energy burn-off load resistor 142 is similar in function to the amplifier burn-off load resistor 130 as discussed hereinabove.

Hot switch relay 125 and transfer switch 140, when switching from Positions A to Positions B, appears as open circuits to the circulator 135. During and after switching occurs, the circulator 135 clears the system of any residual power left in the system by directing the residual power into the reflected energy burn-off load resistor 142.

In addition, when hot switch relay 125 switches from Position A to Position B energy from dual directional coupler 145 and the DUT 115 is directed through the transfer switch 140, to the circulator 135 and is dissipated by the reflected energy burn-off load resistor 142. With the hot switch relay 125 and the transfer switch 140 both in Position B the MRT 100 connects to the DUT 115 and performs active measurements thereof. Interaction between the hot switch relay 125, the transfer switch 140 and active testing of the DUT 115 is further described hereinbelow.

Transfer switch 140 provides sufficient electrical isolation between the measurement system and the microwave energy delivery system. In Position A, the high power microwave energy signal is received on Port 4, passed to Port 3 and to the directional coupler 145. The precision network analyzer 150, connected to Port 2 of the transfer switch 140, connects the transfer switch load resistor 155 on Port 1. In Position B, energy received on Port 4 is passed to Port 1 and dissipated by the transfer switch load resistor 155, and the precision network analyzer 150 on Port 2 is connected to through Port 3 to the directional coupler 145 and the DUT 115. The transfer switch 140 maintains electrical isolation between Ports 4 and 2 (and electrical isolation between the high power microwave energy and the precision network analyzer 150) regardless of the transfer switch 140 position.

In operation, microwave energy is switched to the amplifier burn-off load resistor 130 by the hot switch relay 125 before the transfer switch 140 switches from Position A to Position B. As such, the transfer switch 140 does not operate as a "hot switch" because it is not under a load from the signal generator 105 or amplifier 110 when switching occurs.

One suitable device that may be used as a transfer switch 140 is a TNH1D31 coaxial transfer switch sold by Ducommun of Carson Calif. The TNH1D31 displays less than 1.05 VSWR, better than 0.1 dB insertion loss and less than 80 dB electrical isolation for all states at 915 MHz. The hot switch relay 125 switches out the high energy microwave energy signal before the transfer switch 140 transitions, therefore, transition times for the transfer switch 140 are not critical. High-to-low transition times for the TNDH1D31 are about 75 ms and low-to-high transitions times are about 25 ms.

Directional coupler 145 may be configured to operate like most conventional directional couplers known in the available art. As illustrated in FIG. 1, directional coupler 145 passes the high power microwave energy signal received on Port 1 to Port 2 with minimal insertion loss. Energy reflected back from the DUT 115 and received on Port 2 of the directional coupler 145 is passed through the transfer switch 140 to Port B of the circulator 135. Energy received from the transfer switch 140 on Port B of the circulator 135 is passed to Port C of the circulator 135 and dissipated by the reflected energy burn-off load resistor 142.

Directional coupler 145 samples a small portion of each of the signals received on Port 1 and Port 2 and passes a small portion of the signals to Ports 3 and 4, respectively. The signals on Port 3 and 4 are proportional to the forward and reverse power, respectively. The measurement system measures the signal samples and provides the measurements to the supervisory control system.

Directional coupler 145 samples a small portion of each of the signals received on Port 1 and Port 2 and passes a small portion of the signals to Ports 3 and 4, respectively. The signals on Port 3 and 4 are proportional to the forward and reverse power, respectively. The measurement system measures the signal samples and provides the measurements to the CPU 120. The forward and reverse power measurements from the directional coupler 145 are passively measured and the samples may be taken continuously or at a periodic sample frequency. Unlike the broadband scattering parameter measurements, the directional coupler 145 measurements are indirect measurements of the delivered energy. As such, the measurements from the directional coupler 145 are limited to the bandwidth of the microwave energy supplied to the ablation device 115 from the signal generator 100 (i.e., feedback is fixed to the frequency of the high power microwave energy signal). A single frequency measurements, or narrowband measurement, can be used to calibrate amplitude and phase at a single frequency. By calibrating and/or compensating for the return loss to the antenna feedpoint and phase for 'open' or 'short' we are able to obtain a characteristic representation of the antenna's behavior (i.e., a Smith Chart representation of the antenna behavior).

One suitable directional coupler 145 is a directional coupler sold by Werlatone of Brewster, N.Y. The directional coupler 145 may be a 40 dB dual directional coupler with 30 dB directivity and less than 0.1 dB insertion loss from 800 MHz to 3 GHz.

DUT 115 includes a microwave ablation device that connects to Port 2 of the directional coupler 145 and may be any suitable microwave device capable of delivering microwave energy to tissue. DUT 115 may also include the tissue or surrounding medium in which the microwave ablation device is inserted or deployed.

Supervisory control system includes a central processor unit 120 (CPU) capable of executing instructions and/or performing algorithms, configured to receive one or more inputs and may be configured to control one or more devices in the MRT 100. Inputs may include analog inputs, such as, for example, signals from the forward and reverse coupling ports, Port 3 and Port 4 of the directional coupler 145, respectively. Inputs may also include digital inputs, such as, for example, communication with one or more devices (i.e., precision network analyzer 150).

CPU 120 may control one or more components of the MRT 100. The signal generator 105 may receive at least one of an enabled/disabled control signal from the CPU 120 and reference signal. Enable/disable control signal indicates that the MRT system is in a condition to receive a microwave signal (i.e., the hot switch relay 125 and/or the transfer switch 140 are in a suitable position to receive a microwave signal). Reference signals may include the desired microwave frequency and a gain setting. CPU 120 may also provide control signals to the precision network analyzer 150.

The functionality of the measurement system may be performed in the CPU 120 and the precision network analyzer 150. As illustrated in FIG. 1, the CPU 120 receives the passive inputs of power measurements (i.e., forward and reflected power signals from the directional coupler 145) and the precision network analyzer 150 performs active measurements of the DUT 115.

The measurement system may include other inputs, such as, for example, temperature sensors, cooling fluid temperature or flow sensors, movement sensors, power sensors, or electromagnetic field sensors. For example, an array of temperature sensors (not shown) configured to measure tissue temperature surrounding the DUT may be connected to the CPU 120 or the precision network analyzer 150. Tissue temperatures may be used to generate an estimation of an ablation size or to generate an alarm or fault condition. Cooling fluid temperature or flow sensors may be used to indicate proper operation of a cooled DUT 115.

In another embodiment, the CPU 120 or precision network analyzer 150 may include all of the functionality of the supervisory control system, measurement system or any combination thereof. For example, in another embodiment of the present disclosure, as disclosed hereinbelow, the precision network analyzer 150 may receive the passive inputs, performs the active measurements and then report information to the supervisory system.

In yet another embodiment, the precision network analyzer 150 is part of a modular system, such as, for example, a PXI system (PCI eXtensions for Instrumentation) fold by National Instrument of Austin, Tex. A PXI system (not shown) may include a chassis configured to house a plurality of functional components that form the MRT 100 and connect over a CPI backplane, across a PCI bridge or by any other suitable connection.

Precision network analyzer 150 of the measurement system may connect to Port 2 of the transfer switch 140. Precision network analyzer 150 may be any suitable network analyzer capable of performing scattering parameter measurements of the DUT and/or determining loss information for transmission system. Alternatively, precision network analyzer 150 may be a computer or programmable controller containing a module, program or card that performs the functions of the precision network analyzer 150.

In the embodiment in FIG. 1, precision network analyzer 150 is a stand-alone device or member that is in operative communication with transfer switch 140 and/or CPU 120. In another embodiment, the functionality of the precision network analyzer 150 may be an integral part of the supervisory control system (i.e., a function of the CPU 120).

Precision network analyzer 150 may function in a fashion similar to most conventional network analyzers that are known in the available art. That is, precision network analyzer 150 may determine various properties that are associated with the energy delivery system of the MRT 100, such as, for example, the transmission line, the DUT 115 or the medium surrounding the DUT 115 (i.e., tissue). More particularly, the precision network analyzer 150 determines at least one property or conditions associated with increases in reflected energy (i.e., properties that can be correlated to reduction in energy transmission or decreases in overall system efficiency, such as, a change in the characteristic impedance ($Z_o$) of at least a portion of the microwave energy delivery system). One suitable precision network analyzer 150 is a four port precision network analyzer sold by Agilent of Santa Clara, Calif.

Precision network analyzer 150 may connect to the transfer switch 140 through an attenuator 160 or other suitable protection device. In another embodiment attenuator 160 may scale the signal from the transfer switch 140 to one of a suitable power, current and voltage level.

Attenuator 160 may be a limiting device, such as, for example, a fuse-type device that opens a circuit when a high power signal is detected. Limiting device may appear transparent to the precision network analyzer 150 until the limiting device is hit with a high power signal. One such device is a power limiter sold by Agilent of Santa Clara, Calif., that provides a 10 MHz to 18 GHz broadband precision network analyzer input protection from excess power, DC transients and electrostatic discharge. The attenuator 160 limits RF and microwave power to 25 dBm and DC voltage to 30 volts at 25° C. at 16 volts at 85° C. with turn-on times of less than 100 picoseconds.

Limiting device may function as one of a fuse and a circuit-breaker type device. Fuse device may need to be removed and replaced after failure while a circuit-breaker type device may include a reset that reinitializes the circuit breaker after a failure. Reset may be a manual reset or MRT 100 may include a reset circuit that is initiated and/or performed by the supervisory control system or the like.

In an energy delivery mode, as illustrated in FIG. 1, the MRT 100 is configured to delivery energy to the DUT 115. The microwave energy signal from the signal generator 105 and amplifier 110 passed between the hot switch relay 125 in Position A, the circulator 135, the transfer switch 140 in Position A, the directional coupler 145 and the DUT 115. The measurement system (i.e., the CPU 120) passively measures forward and reflected energy at Port 3 and 4 of the dual directional coupler 145. The precision network analyzer 150 is electrically isolated from the high energy microwave signal by the transfer switch 140.

In another embodiment of the present disclosure, electrical isolation between the ports of the transfer switch 140 allows a portion of the signal at Ports 3 and 4 to pass to Ports 1 and 2 wherein the passed signal is proportional to the high energy microwave signal from the signal generator 105 and amplifier 110. The energy of the passed signal is either sufficiently attenuated by the transfer switch 140 to prevent damage the precision network analyzer 150 or the precision network analyzer 150 may be protected from excessive energy, (i.e., transients and current or voltage spikes) by the attenuator 155, or alternatively, a limiter. The passed signal is shunted to a matched or a reference load and dissipated, through the transfer switch load resistor 155 connected to Port 1 and measured at Port 2 by the precision network analyzer 150.

Precision network analyzer 150 may be configured to passively measure the forward and reflected voltages from the directional coupler 145 and the energy waveform from transfer switch 140. Power parameters, including the magnitude and phase of the microwave signal, may be obtained or calculated from the measured signals, by conventional algorithms or any suitable method known in the available art. In one embodiment, the forward and reflected measurements of power and phase can be used to determine impedances and admittances at a given frequency using a Smith Chart.

In another embodiment, the impedance at the MRT 100 may be calculated as follows: First, the forward and reflected voltages, $V_{fwd}$ and $V_{ref}$, respectively, are measured. Then, the voltage standing wave ratio ($V_{SWR}$) may be calculated using the equation:

$$V_{SWR} = \frac{V_{fwd} + V_{ref}}{V_{fwd} - V_{ref}}$$

The magnitude of the load impedance ($Z_L$) may be determined by first computing the reflection coefficient, $\Gamma$, from $V_{SWR}$ using the following equation:

$$|\Gamma| = \frac{V_{SWR} - 1}{V_{SWR} + 1}$$

Then, based on intrinsic system impedance, the load impedance $Z_L$ is:

$$Z_L = \frac{Z_0(1 + \Gamma)}{(1 - \Gamma)}$$

Phase must be determined by the measured phase angle between the forward and reflected signals.

Those skilled in the relative art can appreciate that the phase may be determined with calibrated or known reference phases (e.g., measurements with a short or open at the antenna feedpoint) and with measured values of $V_{fwd}$ and $V_{ref}$. The magnitude and the phase of $Z_L$ can then be communicated or relayed to the supervisory control system that may be designed to make adjustments to the MRT as discussed hereinbelow.

Figure 2:
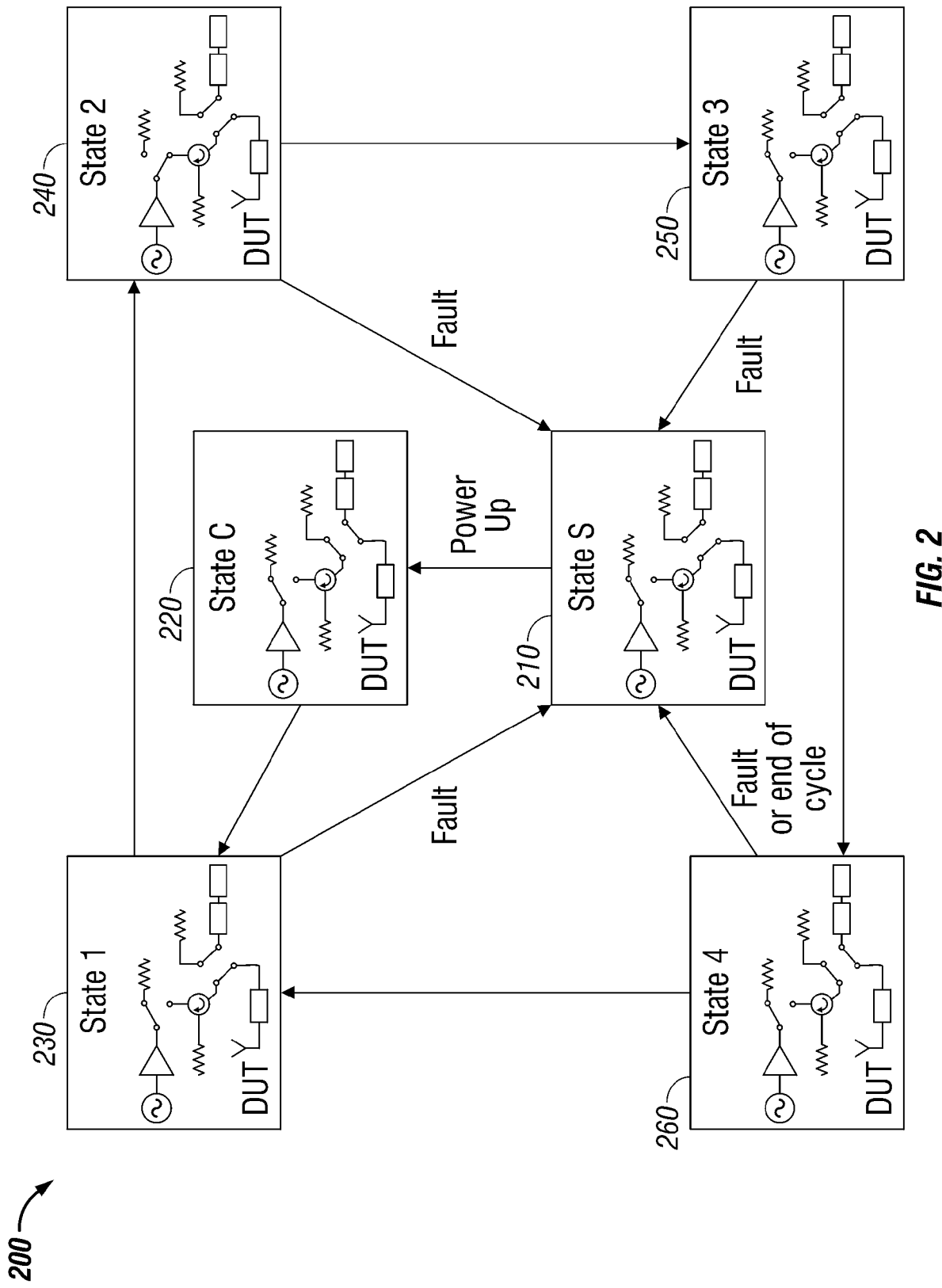
FIG. 2 is a state machine functional block diagram of the microwave energy delivery, measurement and control system of FIG. 1.

FIG. 2 displayed the MRT system state machine 200. The six states, defined as State S, State C and States 1-4, show the various states of the MRT 100 in FIG. 1 and are designated as 210-260, respectively. The operating states of the MRT 100 of FIG. 1 are determined by the position of the two switches, the hot switch relay 125 and the transfer switch 140, and the previous operating state of the MRT 100. In use, the operation of the MRT 100 flows between the six states. Multiple states end in the same switch orientation but are shown as different states to illustrate a unique control sequence. The utility of each state during the ablation cycle are described hereinbelow.

State S 210 is the Standby State 210 of the MRT. When power is removed both switches 125, 140 default to this condition, therefore, this condition is also the failsafe position (i.e., the default condition when power is removed or on power failure directs energy away from the patient or medical personnel). As such, the system provides for safe operation in the case of power failure, fault detection or when the system is not in use. A failsafe Standby State 210 also ensures that on startup, transient power spikes or other potentially dangerous power surges from the amplifier 110 are directed into the amp burn-off matched load resistor 130 thereby protecting equipment downstream from the hot switch relay 125.

State C 220 is the Calibration State 220 of the MRT. During the Calibration State 220 the hot switch relay 125 directs microwave power from the signal generator 105 and amplifier 110 to the amp burn-off load resistor 130 and the transfer switch 140 connects the precision network analyzer 150 to the DUT 115. One or more calibrations are performed during this state. In one first calibration the precision network analyzer 150 may be calibrated to the DUT 115 reference plane, through the attenuator 160, transfer switch 140 and directional coupler 145, for broadband scattering parameter measurements. A second calibration may involve the measurement of line attenuation between the directional coupler 145 output ports and the DUT 115 reference plane. Determining line attenuation may require a second calibration value that may be obtained by replacing the DUT with an 'open' or 'short' at the exact reference path length. Alternatively, a second calibration value may be obtained by operating the antenna in air and comparing this value with a known value of the antenna operating in air. This attenuation value is used to calibrate power measurements at the directional coupler 145 to power delivered to the DUT 115. An initial broadband scattering parameter measurement may be made during the Calibration State 220 to capture the DUT 115 impedance within uncooked tissue.

State 1 130 begins post calibration or after State 4 260. During State 1 130, the transfer switch 140 is activated which connects the DUT 115 load to Port 2 of the circulator 140 and the precision network analyzer 150 to the terminal switch load resistor 155. In State 1 230, the only high power signal present in the system is flowing between the signal generator 105, the amplifier 110, the hot switch relay 125 in Position B and the amplifier burn-off resistor 130. State 1 230 may include a delay to ensure that the transfer switch 140 has transitioned from Position B to Position A. A fault condition in State 1 230 returns the system to State S 210, the Standby State 210.

State 2 240 begins after the transfer switch 140 has completed the transfer switch's 140 switching cycle in State 1 230. A high control signal, delivered to the hot switch relay 125 from the CPU 120, directs power from the signal generator 105 and amplifier 110 through the circulator 135, transfer switch 140, directional coupler 145 and into the DUT 115. State 2 240 is the period during which an ablation is generated and generally represents the majority of system time. A fault condition in State 2 240 returns the system to State S 210, the Standby State 210.

State 3 250 ends a period of power delivery to the DUT 115 in preparation for a precision network analyzer 150 scattering parameter measurement. A low signal is presented to the hot switch relay 125 directing power from the signal generator 105 and amplifier 110 into the amplifier burn-off load resistor 130. A period of clear line wait time is added to the end of State 3 to allow the system to clear the circuit of high power signals. A fault condition in State 3 returns the system to State S, the Standby State 210.

State 4 260 is initiated after the clear line wait time at the end of State 3 250 expires. State 4 260 is initiated by activating the transfer switch 140. Activation of the transfer switch 140 restores the system to the calibration configuration allowing the precision network analyzer 150 to perform broadband scatter parameter measurement of the DUT 115. The only high power signals present in the system flow between the signal generator 105, the amplifier 110, the hot switch relay 125 and the amplifier burn-off load resistor 130. After the precision network analyzer 150 completes a measurement cycle the system leaves State 4 260, re-enters State 1 230, and the MRT 100 repeats the cycle unless the ablation cycle has ended or a fault occurs, in which case the system enters State S 210, the Standby State 210.

The MRT system state machine 200 essentially eliminates the risk of high power signals from potentially damaging sensitive microwave equipment, such as, for example, the precision network analyzer 150. Additional switching and clear line delay times may be added into the system to ensure this safety aspect of the system architecture.

Figure 3:
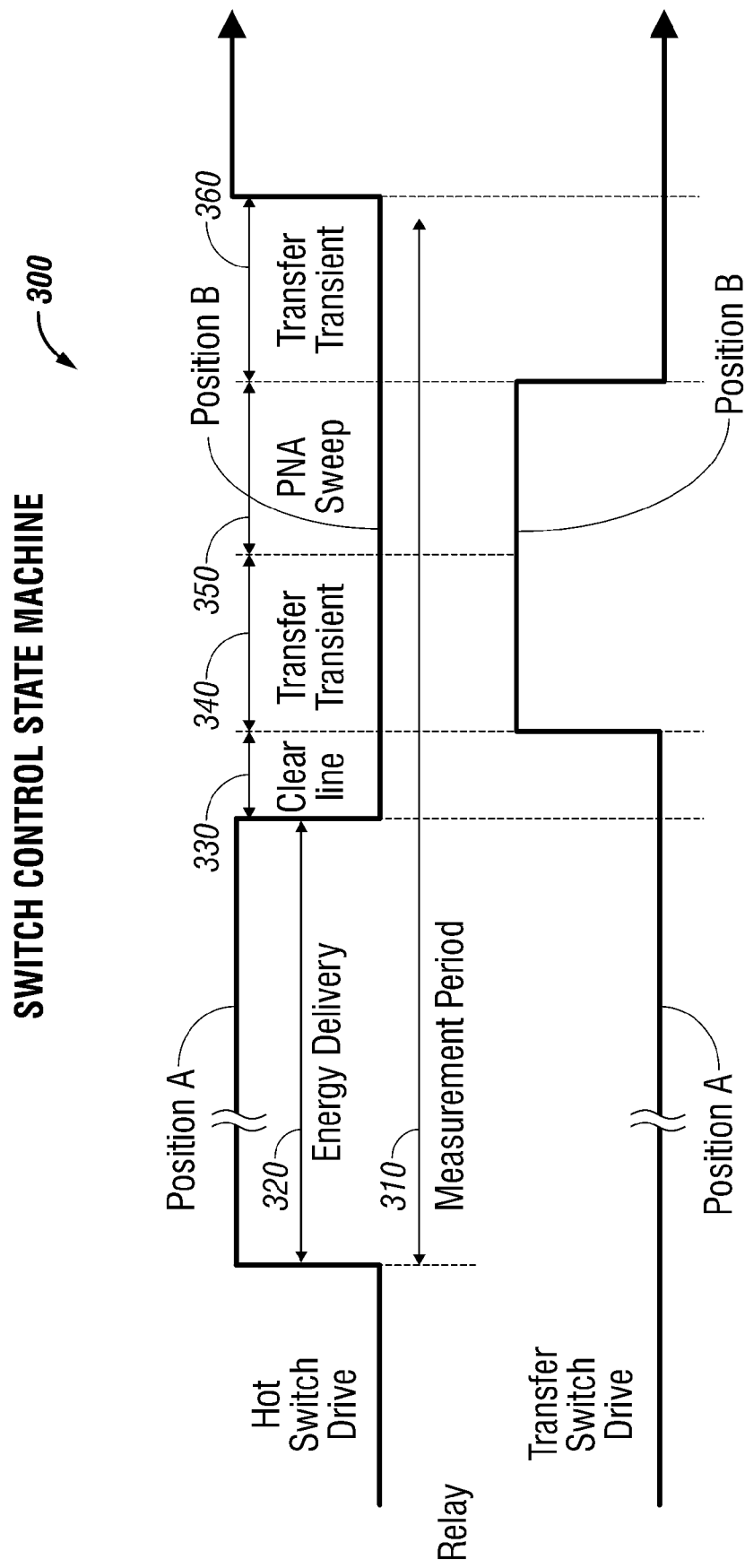
FIG. 3 is a switch control state machine for the microwave energy delivery, measurement and control system including a precision network analyzer.

FIG. 3 is a switch control state machine 300 for the microwave energy delivery, measurement and control system of the present disclosure. With reference to FIG. 1, the position of the hot switch relay 125 is indicated in the upper timing diagram of FIG. 3 and the position of the transfer switch 140 is indicated in the lower timing diagram. A measurement period 310 includes an energy delivery period 320, a clear line period 330, a first transfer transient period 340, a precision network analyzer sweep period 350 and a second transfer transient period 360. The energy delivery period 320 is the period in which energy is delivered to the DUT 115 and initializes the start of a new measurement period 310. The clear line period 330, which follows the energy delivery period 320, provides a delay in which the standing waves and transients in the system are allowed to dissipate through the circulator 135 and load 142 or the DUT 115. The first transfer transient period 340 provides a delay to allow the transfer switch 140 to transition from Position A to Position B. The precision network analyzer sweep period 350 provides time for the precision network analyzer 150 to perform broadband scattering parameter measurements. The second transfer transient period 360 provides a delay to allow the transfer switch 140 to transition from Position B to Position A.

The time intervals of the timing diagrams in the switch control state machine 300 of FIG. 3 are not necessarily to scale. For example, if the system is providing a continuous waveform, the energy delivery period 320, or the "on-time" in which microwave energy is delivered to the DUT 115, is a majority of the measurement period 310. The remaining portion of the measurement period 310, or "off-time", is split between the clear line period 330, the first transfer transient period 340, the precision network analyzer sweep period 350 and second transfer transient periods 360. The clear line period 330 and the first and second transfer transient periods 340, 360 may be fixed in duration and based on the specific hardware used in the MRT system 100. The precision network analyzer sweep period 350 is based on one or more sampling parameters. Sampling parameters include the sweep bandwidth, the number of steps within the bandwidth, the number of samples taken at each step and the sampling rate.

The clear line period 330 must be sufficient in duration to allow all transients in the system to dissipate after the hot switch relay 125 switches from Position A to Position B. Transient, such as, for example, standing waves or reflective energy, may "bounce" between components before eventually being dissipated or shunted by the reflected energy burn-off load resistor 142, dissipated in the system 100, or expended by the DUT 115. For example, the hot switch relay 125 may switch from Position A to Position B in as little as about 360 ns, thereby leaving energy in the MRT 110 between the circulator 135 and the DUT 115. The energy may be sufficiently high to damage the precision network analyzer 150 if energy is not dissipated.

After switching occurs energy remains in the system for an amount of time. The amount of time is related to the cable length, or path distance, between the antenna and the hot switch relay 125. For a typical system using conventional cables having a transmission line with a dielectric value (∈) of about 2, the signal speed is about 1.5 ns/ft for each direction. For example, a circuit and cable length of about 10 feet between the DUT and the switch, a signal traveling away from the hot switch relay 125 would travel once cycle, or the 20 feet between the hot switch relay 125, the DUT 115 and back to the hot switch relay 125, in about 30 ns. Without dissipating the standing waves, the signal may ringing, or remain in the system, for as many as 5 cycles between the hot switch relay 125 and the DUT 115, or about 150 ns. Circulator may dissipate the standing waves to an acceptably low energy level in as little as one or two cycles between the DUT and the hot switch relay 125. Transfer switch 140 remains in Position A until the energy has dissipated to acceptably low energy levels.

In another embodiment of the present disclosure, the clear line period 330 is variable and determined by measurements performed by the precision network analyzer 150 or the CPU 120. For example, measurements from the forward coupling port (Port 3) or the reverse coupling port (Port 4) of the directional coupler 145 may be used to determine if energy remains in the system. The hardware design, or at low microwave energy levels, the amount of transient energy remaining in the MRT 100 after the hot switch relay 125 transitions from Position A to Position B, may be minimal and may allow the clear line period 330 to be equal to, or about equal to, zero.

First transfer transient periods 340 provide a delay before initiating the precision network analysis sweep 350. The first transfer transient period 340 allows the transfer switch 140 to switch from Position A to Position B before the precision network analyzer 150 begins the broadband scattering parameter sweep.

Second transfer transient period 360 provides a delay before the subsequent measurement period begins (i.e., the next energy delivery period). The second transfer transient period 360 allows the transfer switch 140 to switch from Position B to Position A before the hot switch relay 125 transitions from Position B to Position A and energy delivery to the DUT 115 resumes.

During the precision network analyzer sweep 350, the precision network analyzer 150 determines broadband small-signal scattering parameter measurements. The sweep algorithm, and the amount of time to perform the sweep algorithm, is determined by the specific control algorithm executed by the CPU 120. Unlike the passive forward and reflected power measurements, the measurements taken during the precision network analyzer sweep period 350 are active measurements wherein the precision network analyzer 150 drives the DUT 115 with a broadband signal and measures at least one parameter related to the signal (i.e., $S_{11}$, reflection coefficient, reflection loss). The CPU 120 uses at least one of an active measurement taken by the network analyzer 350 during the broadband small signal scattering parameter measurements or a passive measurements from the directional coupler 145 in a feedback algorithms to control further energy delivery and/or subsequent MRT 100 operation.

Energy delivery time, or "on-time", as a percentage of the measurement period, may be adjusted. For example, the initial duration of the energy delivery may be based on historical information or based on at least one parameter measured during the calibration or start-up states, 220 210, discussed hereinabove. The "on-time" may be subsequently adjusted, either longer or shorter, in duration. Adjustments in the "on-time" may be based on the measurements performed by one of the precision network analyzer 150 and the CPU 120, from historical information and/or patient data. In one embodiment, the initial duration of an energy delivery period 320 in the ablation procedure may be about 95% of the total measurement period 310 with the remaining percentage, or "off-time", reserved for measurement ("on-time" duty cycle approximately equal to about 95%). As the ablation procedure progresses, the "on-time" duty cycle may be reduced to between 95% and 5% to reduce the risk of producing tissue char and to provide more frequent measurements. The "off-time" may also be used to perform additional procedures that provide beneficial therapeutic effects, such as, for example, tissue hydration, or for purposes of tissue relaxation.

Figure 4:
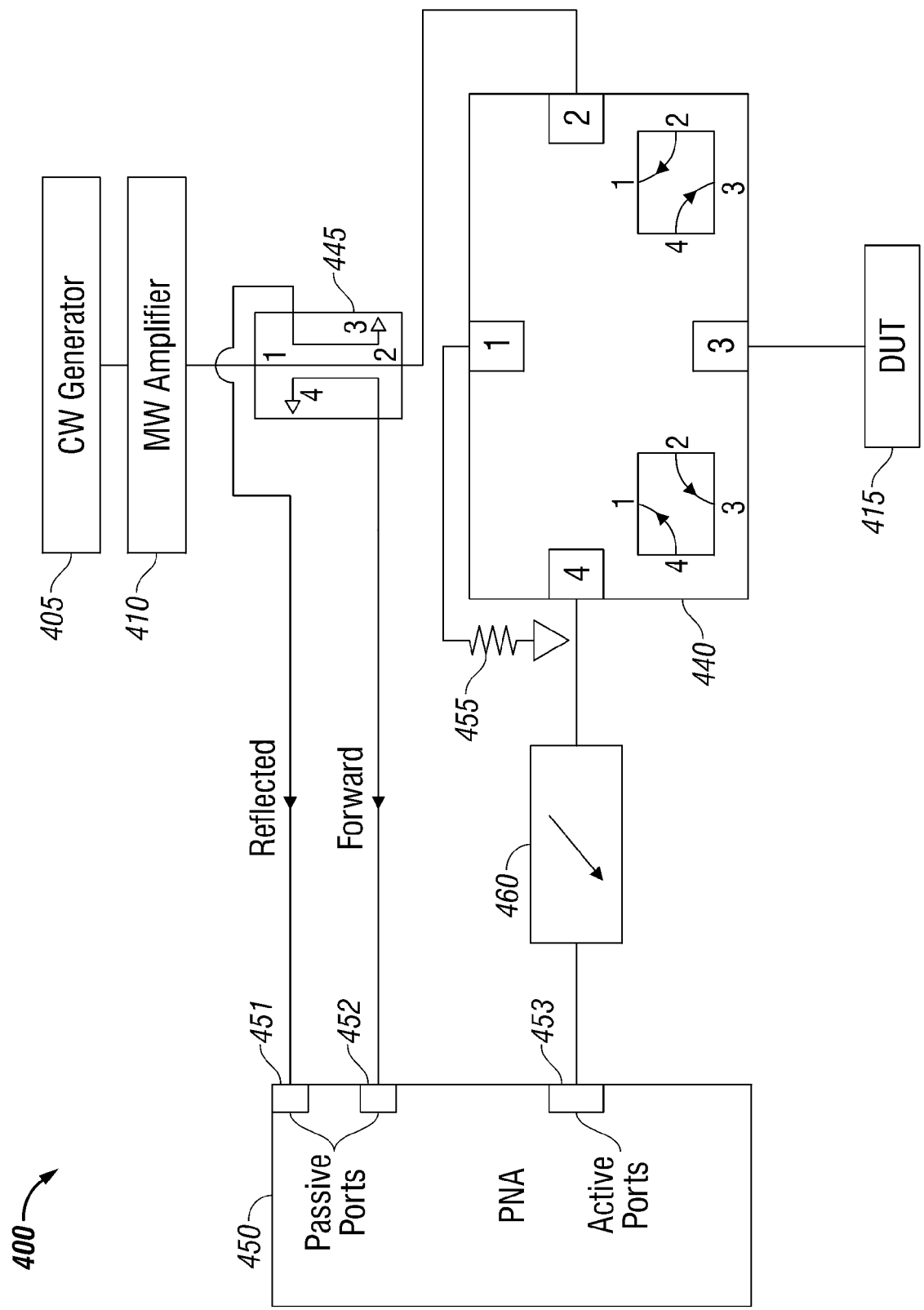
FIG. 4. is a functional block diagram of a precision network analyzer including passive and active measurements.

In another embodiment of the present disclosure, as illustrated in FIG. 4, the MRT 400 includes a signal generator 405, a microwave amplifier 410, a directional coupler 445, a transfer switch 440, a terminator 455, an attenuator 460, a precision network analyzer 450 and a DUT 415. In the present embodiment, the precision network analyzer 450 performs active and passive measurements of various system parameters of the MRT 400.

MRT 400 includes a signal generator 405 and amplifier 410 to generate and supply a high energy microwave signal to the directional coupler 445. In an energy delivery mode the directional coupler 445 passes the signal to Port 2 of the transfer switch 440 and the transfer switch 440 passes the signal to the DUT 415 through Port 3. In a measurement mode, the high energy microwave signal is passed to a terminator 455 connected to Port 1 of the transfer switch 440. Precision network analyzer 450 connects the first and second passive ports 451, 452 to the forward and reflected power ports, Ports 3 and 4, of the directional coupler 445, respectively. The active port 453 of the precision network analyzer 450 connects to Port 4 of the transfer switch 440. Precision network analyzer 450 may connect to Port 4 of the transfer switch 440 through a suitable attenuator 460 as illustrated in FIG. 4 and discussed hereinabove.

In an energy delivery mode, the precision network analyzer 450 of the MRT 400 passively measures forward and reflected power of the high energy microwave signal from the forward and reflected power ports, Ports 3 and 4, respectively, of the directional coupler 445.

In a measurement mode, the precision network analyzer 450 of the MRT 400 actively performs broadband scattering parameter measurements by connecting to the DUT 415 through Ports 3 and 4 of the transfer switch 440. The precision network analyzer 450 drives the DUT 415 with a signal at a range of frequencies and measures at least one parameter related to the DUT 415 at a plurality of frequencies.

Transfer switch 440 may be a single-pole, dual-throw coaxial switch that provides sufficient electrical isolation between Port 2 and Port 4 of the transfer switch 440 thereby preventing the high energy signal from damaging the precision network analyzer 450 in either the energy delivery mode, the measurement mode and while switching therebetween. Attenuator 460 provides sufficient signal attenuation to prevent the high energy signal from damaging the precision network analyzer 450. Alternatively, attenuator 460 may be a limiting-type device as discussed hereinabove.

Figure 5:
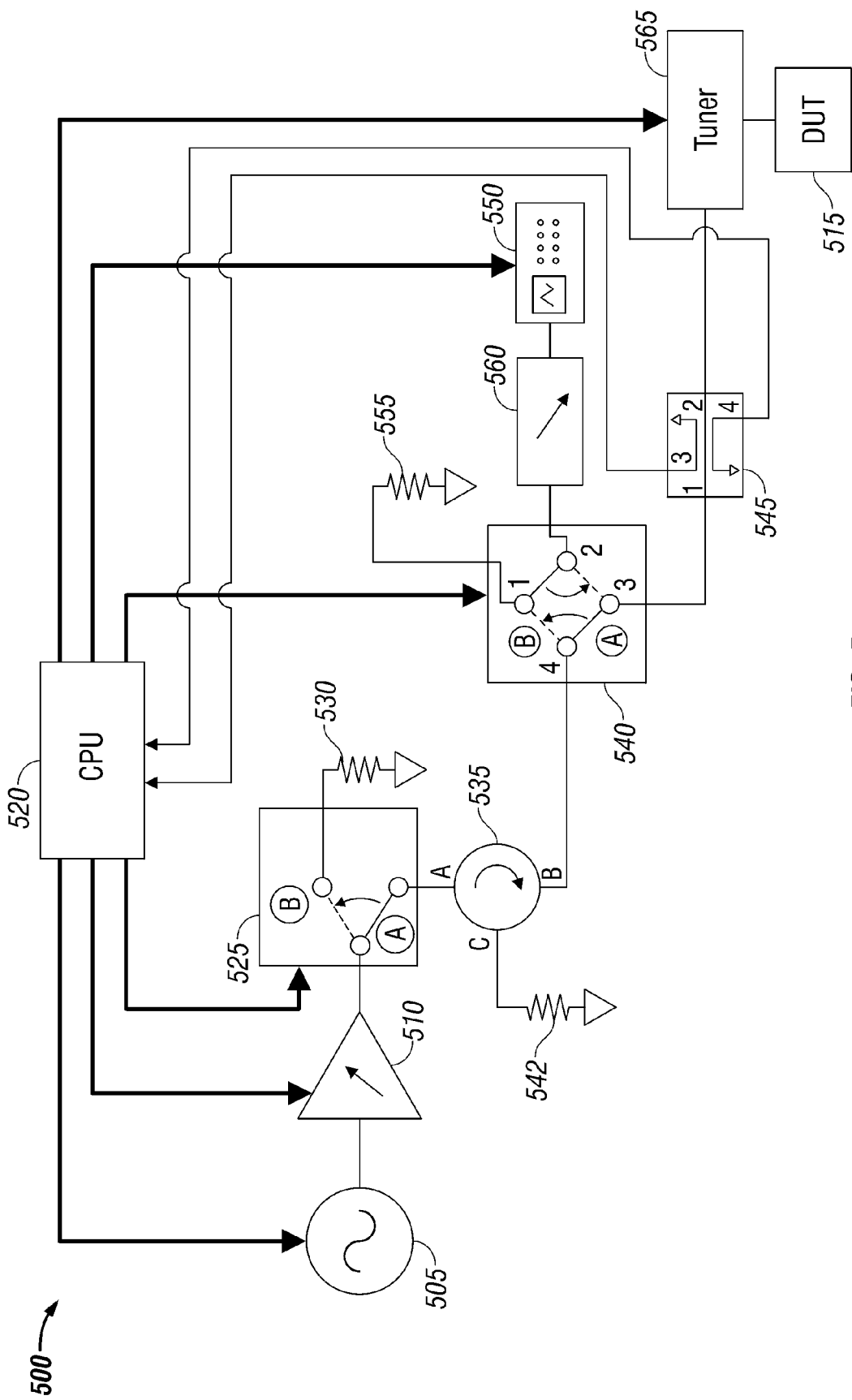
FIG. 5 is a functional block diagram of a microwave energy delivery, measurement and control system including an impedance tuner.

In yet another embodiment of the present disclosure, as illustrated in FIG. 5, the MRT 500 includes a signal generator 505, an amplifier 510, a CPU 520, a hot switch relay 525, an amplifier burn-off load resistor 530, a circulator 535, a transfer switch 540, an attenuator 560, a precision network analyzer 550 and a tuner 565 positioned between the dual directional coupler 545 and the DUT 515. The tuner 565 may be a tuning network or tuning circuit configured to match the impedance of the delivery system with the impendence of the DUT 515 or, alternatively, the tuner 565 is configured to match the impedance of the DUT 515 to the impedance of the delivery system. Tuner 565 may include a variable stub tuning network, a diode network or any other automated tuning network or circuit capable of high power operation and having the ability to match the DUT 565 impedance variations to the MRT 500 system impedance over the cooking cycle.

In calculating a tuner adjustment, the CPU 520 characterizes the tuner 565 and removes the tuner 565 from the signal measured in the active measurement portion of the measuring cycle.

Tuner 565 may be incorporated into the DUT 515 wherein the CPU 520 directs the tuner 565 to actively changes one or more properties of the antenna (not shown) in the DUT 515 such that the antenna impedance appears to be about equal to a characteristic impedance, e.g. 50 Ohms. For example, the CPU 520 may instruct the tuner 565 to change the effective antenna length or change one or more dielectric properties.

The CPU 520 may use feedback from the measurement system to optimize energy delivery to the DUT 515 during at least a portion of the ablation procedure. Optimization may include: changing the frequency of the delivered microwave energy to better match the impedance of the DUT 515, using the tuner 565 to adjust the output impedance of the MRT 500 to match the impendence of the DUT 515 or a combination thereof.

In one embodiment the supervisory control system uses a forward power measurement from directional coupler 545, a reverse power measurement from the directional coupler 545, or one or more broadband scattering perimeter measurements to optimize energy delivery.

Figure 6:
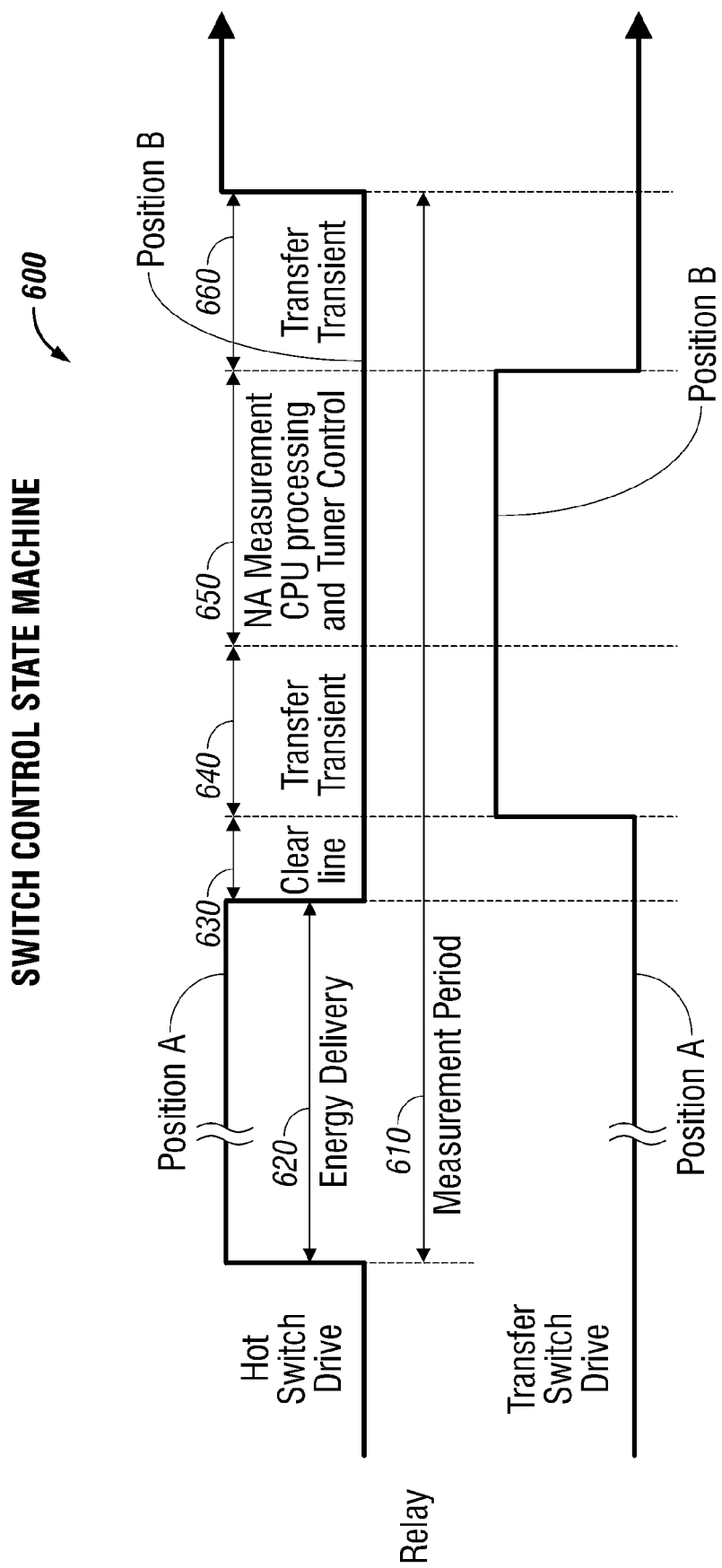
FIG. 6 is a switch control state machine for the microwave energy delivery, measurement and control system including a precision network analyzer, CPU and a tuner.

FIG. 6 is a switch control state machine 600 for the microwave energy delivery, measurement and control system 500 illustrated in FIG. 5. The position of the hot switch relay 525 is indicated in the upper timing diagram and the position of the transfer switch 540 is indicated in the lower timing diagram. A measurement period 610 includes an energy delivery period 620, a clear line period 630, a first transfer transient period 640, a measurement, CPU processing and tuner control period 650 and a second transfer transient period 660. The clear line period 630 is after the energy delivery period 620 and provides a delay in which the standing waves and transients in the MRT 500 are allowed to dissipate. The first transfer transient period 640 provides a delay to allow the transfer switch 540 to transition from Position A to Position B. The measurement, CPU processing and tuner control period 650 allows the precision network to perform broadband scattering parameter measurements, perform control algorithms in the CPU and to perform adjustments to system tuning. The second transfer transient period 660 provides a delay to allow the transfer switch 540 to transition from Position B to Position A.

The time intervals of the timing diagrams in the switch control state machine 600 of FIG. 6 are not to scale. For example, the energy delivery period 620, or "on-time" in which microwave energy is delivered to the DUT 515, is typically equal to a majority of the measurement period 610. The remaining portion of the measurement period, or "off-time", is split between the clear line period 630, the first transfer transient period 640, the measurement, CPU processing and tuner control period 650 and second transfer transient periods 660. The clear line period 630 and the first and second transfer transient periods 640, 660, respectively, may be fixed in duration and based on specific hardware in the system. The measurement, CPU processing and tuner control period 650 is based on the sampling parameter, processing time or tuner control time. Sampling parameters include the sweep bandwidth, the number of steps within the bandwidth, the number of samples taken at each step and the sampling rate. The CPU processing includes the execution of the tuner algorithm and the tuner control time includes a frequency adjustment, a tuner adjustment or any related system settling time.

The clear line period 630 must be sufficient in duration to allow all transients in the system to dissipate after the hot switch relay 625 switches from Position A to Position B. Transient, such as, for example, standing waves or reflective energy, may "bounce" between components before eventually being dissipated or shunted through the reflected energy burn-off load resistor 642, dissipated in the system, or expended by the DUT 615. For example, the hot switch relay 625 may switch in from Position A to Position B in as little as about 360 ns, thereby leaving energy in the circuit between the circulator 635 and the DUT 615. The energy present in the MRT 500 circuitry and the DUT 515 may be sufficiently high to damage the precision network analyzer 550, therefore, the transfer switch 540 remains in Position A until the energy has dissipated to acceptably low energy levels. As discussed hereinabove, the amount of time for the energy to dissipate is dependent on the circuit and cable length in which the standing waves must travel. In one embodiment (dielectric value, $\in_r=2$) the length of time is equal to:

dissipation time=(2×distance*1.5 ns/ft)*safety factor;

wherein the distance equals the circuit length plus the cable length, safety factor equals 2 or 3 and the speed of 1.5 ns/ft is based upon approximately $\in_r=2$ for typical transmission line cables In another embodiment of the present disclosure, the clear line period 630 is variable and determined by the precision network analyzer 550 or the CPU 520 measurements. For example, measurements from the forward coupling port (Port 3) and the reverse coupling port (Port 4) of the directional coupler 545, may be used to determine if energy remains in the system. The hardware design, or at low microwave energy levels the amount of transient energy remaining in the system after the hot switch relay 625 transitions from Position A to Position B, may be minimal and may allow the clear line period to be equal to, or about equal to, zero.

First transfer transient period 640 provides a delay before initiating the measurement, CPU processing and tuner control period 650. The first transfer transient period 640 allows the transfer switch 540 to switch from Position A to Position B before the precision network 550 begins the broadband scattering parameter sweep.

Second transfer transient period 360 provides a delay before the subsequent measurement period begins (i.e., the next energy delivery period). The second transfer transient period 660 allows the transfer switch 640 to switch from Position B to Position A before the hot switch relay 525 transitions from Position B to Position A and energy delivery to the DUT 515 resumes.

During the measurement, CPU processing and tuner control period, the precision network analyzer 550 determines broadband small-signal scattering parameter measurements. The measurement algorithm is determined by the specific control algorithm used by the supervisory control system and is similar to the precision network analyzer sweep algorithm discussed hereinabove. The supervisory control system, or CPU 520, the active measurements of the broadband small signal scattering parameter measurements or the passive measurements from the directional coupler 545 in a tuning algorithm. The tuning algorithm checks for the presence of a mismatch in impedance between the MRT 500, the DUT 515, and/or any combination thereof, and determines if an adjustment is necessary to correct the impedance mismatch.

Energy delivery time, or "on-time", as a percentage of the measurement period, may be adjusted. For example, the initial duration of the energy delivery may be based on historical information or based on at least one parameter measured during the calibration or start-up states, 220 210, discussed hereinabove. The "on-time" may be subsequently adjusted, either longer or shorter, in duration. Adjustments may be based on the measurements performed by the precision network analyzer 550 and/or the CPU 520 or from historical information and/or patient data. In one embodiment, the initial duration of an energy delivery period in the ablation procedure may be about 95% of the total measurement period with the remaining percentage, or "off-time", reserved for measurement ("on-time" duty cycle approximately equal to about 95%). As the ablation procedure progresses, the "on-time" duty cycle may be reduced to between 95% and 5% to reduce the risk of producing tissue char and to provide more frequent measurements.

The "off-time" may also be used to perform additional procedures that provide beneficial therapeutic effects, such as, tissue hydration, or for purposes of tissue relaxation. For example, tuning algorithm may initiate a re-hydration of tissue to reduce tissue impedance instead of adjusting the frequency or re-tuning the MRT.

Figure 7:
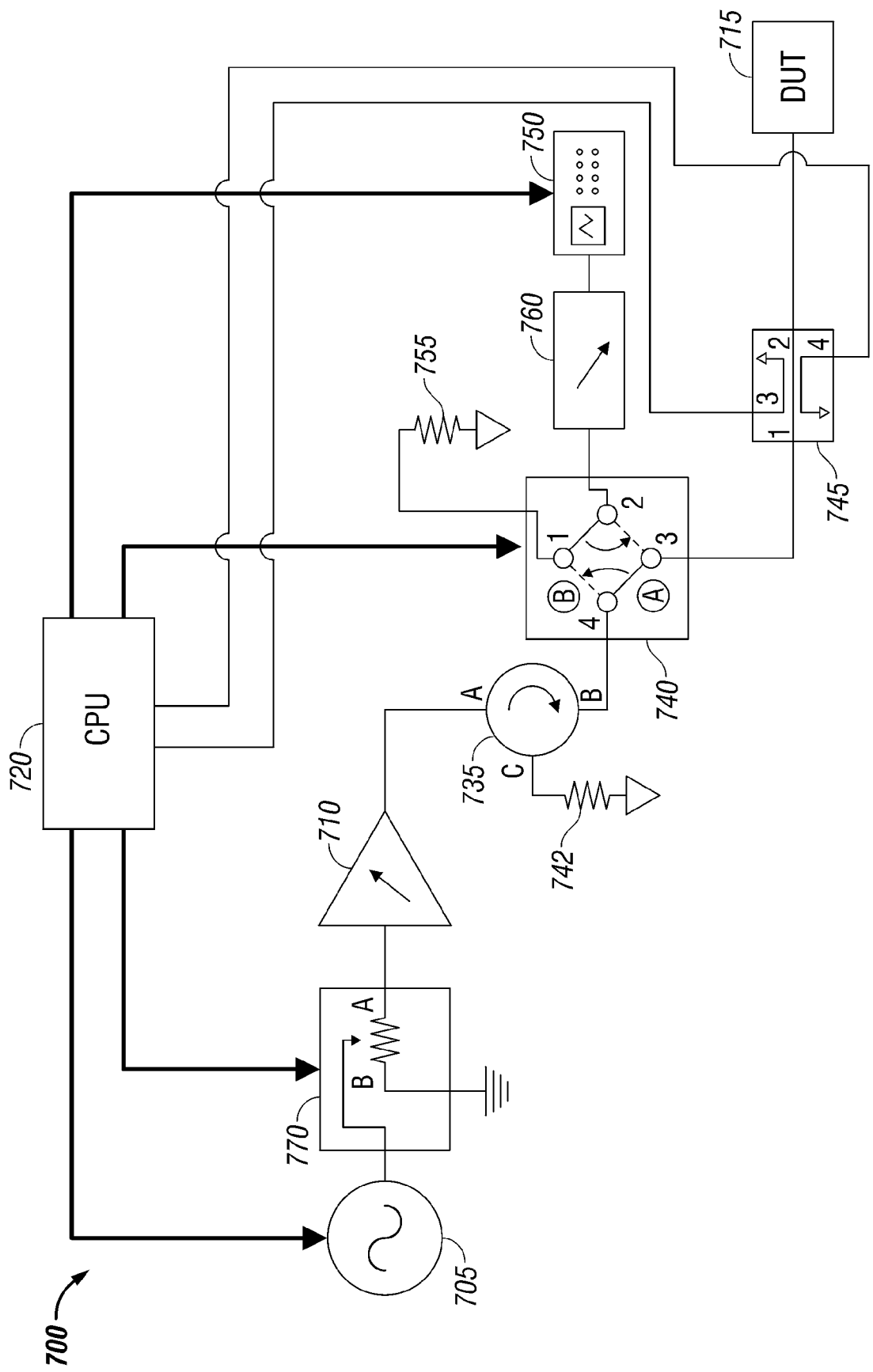
FIG. 7 is a functional block diagram of a microwave energy delivery, measurement and control system according to another embodiment of the present disclosure.

Another embodiment of the MRT is illustrated in FIG. 7 and is shown as MRT 700. MRT 700 includes a variable attenuator 770 that replaces the hot switch relay 125 in the MRT 100 in FIG. 1. In FIG. 7, the MRT 700 includes a signal generator 705, a variable attenuator 770, an amplifier 710, a CPU 720, a circulator 735, a load resistor 742, a transfer switch 740, a transfer switch load resistor 755, an attenuator 760, a precision network analyzer 750, and a directional coupler 745 that connects to the DUT. The signal generator 705 supplies a microwave frequency signal to the variable attenuator 770. Variable attenuator 770 includes a variable network or circuit that scales the signal from the signal generator 705 between 0% and 100% and provides the scaled signal to the amplifier 710. Amplifier 710 amplifies the signal by a fixed amount and provides the signal to the circulator 735.

The MRT 100 in FIG. 1 controls the energy output (i.e., the power of the microwave signal) by adjusting the output of the signal generator 105 and/or the gain of the amplifier 110 (i.e., signal from the signal generator 105 amplified by the gain of the amplifier 710). In the MRT 700 of FIG. 7, the energy output is controlled by one or more of the signal generator 705, the variable attenuator 770 and the amplifier 710. The output energy of the MRT 700 in FIG. 7 is equal to the signal generator 705 output scaled by variable attenuator 770 attenuation percentage and amplified by the gain of the amplifier 710.

With reference to the hot switch relay 125 in FIG. 1 and the variable attenuator 770 in FIG. 7, Position A of the hot switch relay 125 is equivalent to the variable attenuator 770 is Position A (i.e., a scaling factor of 100%). In both FIGS. 1 and 7, Position A provides microwave energy to Port A of the circulator 135 and 735, respectively. Similarly, Position B of the hot switch relay 125 is equivalent to the variable attenuator 770 in Position B (i.e., a scaling factor of 0%). Position B in both FIGS. 1 and 7, no microwave energy signal is provided to Port A of the circulator 135 and 735, respectively.

The hot switch relay 125 in the MRT 100 of FIG. 1 includes a switch that switches between Position A and Position B and is capable of executing the transition in a minimum amount of time to prevent transients or spikes in the waveform. The variable attenuator 770 in the MRT 700 of FIG. 7 may includes an automated variable attenuator, such as, for example, a rheostat-like circuit that does not switch but transitions between Position A and Position B thereby generating fewer transients compared to the switch in FIG. 1.

Atenuator activation time would be added to the dissipation time calculation for safe switching and measurement.

In yet another embodiment of the present disclosure, the DUT includes a MRT calibration device configured to measure the length of the transmission path from the antenna feedpoint to the directional coupler and each respective signal to the network analyzer. FIG. 8 is a schematic representation of an ablation device for use in calibrating a microwave energy delivery, measurement and control system of the present disclosure.

As is known in the art, calibration of a microwave energy delivery system may be preformed by various calibration procedures. For example, one of a Short-Open-Load (SOL), a Short-Open-Load-Thru (SOLT), a Short-Short-Load-Thru (SSLT) and a Thru-Reflect-Line (TRL) calibration technique may be used.

In one embodiment the system is calibrated with a Short-Open (SO) calibration technique. The SO calibration provides a determination of the relative performance of the DUT. The Short-Open calibration technique is known in the art and is generally described hereinbelow.

The first step of the SO calibration is preformed by running the microwave generator with a "short" at the output of the microwave generator (i.e., the coaxial cable connector). The second step of the SO calibration is preformed by running the microwave generator with the output of the microwave generator "open". The two steps of the SO calibration, which is often referred to as "shifting a reference plane" allows the generator to analyze the system up to the output of the directional coupler. One shortcoming of performing this calibration by placing the "open" and the "short" at the output of the generator is that the calibration fails to account for any portion of the transmission line beyond the microwave generator.

Figure 8A:
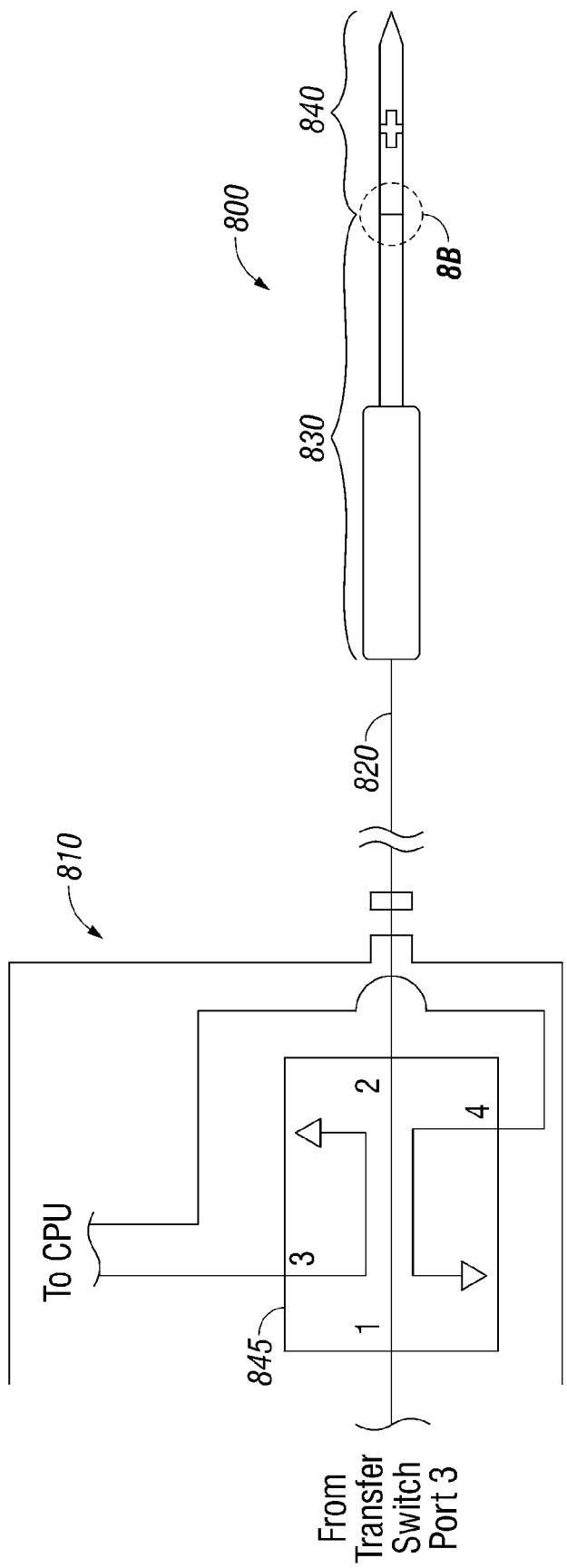
FIG. 8A is a schematic representation of an ablation device for use in calibrating the microwave energy delivery, measurement and control system of the present disclosure.

FIG. 8A illustrates the directional coupler the output of a microwave generator 810 and a coaxial cable 820 that connects the microwave generator 810 to an MRT calibration device 800 of the present disclosure. The MRT calibration device 800 includes a transmission portion 830 and an antenna portion 840.

Figure 8B:
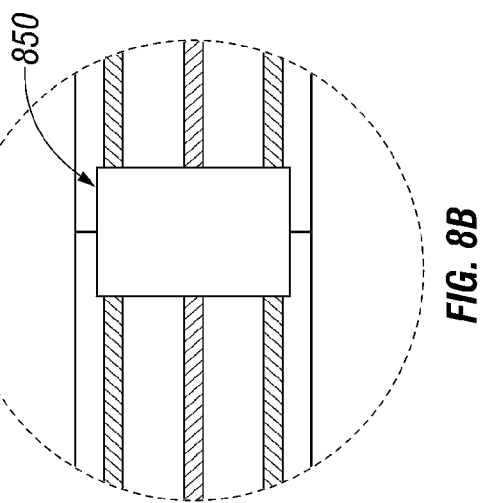
FIG. 8B is a cross-sectional schematic representation of the ablation device and switching mechanism for calibrating the microwave energy delivery device.

FIG. 8B illustrates the transition between the transmission portion 830 and the antenna portion 840. Switching mechanism 850 is located adjacent on the proximal portion of the antenna under test 840 and on the distal portion of the transmission portion 830 of the MRT calibration device 800. Switching mechanism 850 allows the system to perform an SO calibration without replacing the DUT.

Figure 8C:
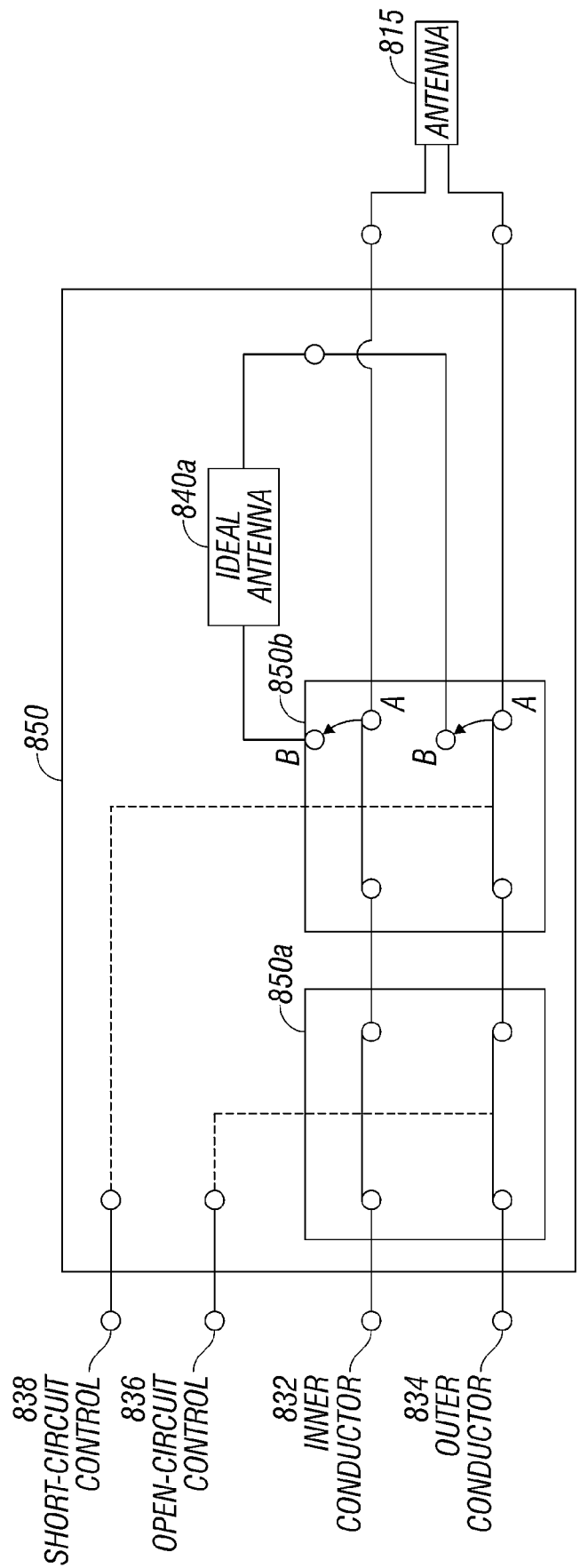
FIG. 8C is an electrical schematic of the switching mechanism of FIG. 8B.

Switching mechanism 850 is further illustrated in FIG. 8C and includes an open circuit switch 850a, a short circuit switch 850b and a short circuit load 840a.

The switching mechanism 850 in the MRT calibration device 800 allows the reference plane to be shifted to a point proximal the antenna thereby accounting for a majority of the transmission path in the calibration procedure. An open circuit is first obtained by the open circuit control 836 actuating the open circuit switch 850a to an open position thereby disconnecting the inner conductor 832 and outer conductor 834 from the antenna under test 815.

A short circuit between the inner conductor 832 and the outer conductor 834 through a short circuit load 840a is obtained by the short-circuit control 838 transitioning the short circuit switch 850b from Position A to Position B. The short circuit load 840a is a fixed load that replaces the antenna under test 815. For example, in one embodiment the short circuit load 840a is an antenna with a feedpoint equivalent to the antenna under test 815 thereby providing a known antenna response that can be used to calibrate the antenna under test 815.

With the short circuit switch 850b in Position B the system yields a known phase and amplitude of the reflected energy at the antenna feed. The antenna under test 840 is replaced with a short circuit load 840b that may include an equivalent path-length and/or an equivalent antenna. Energy provided to the short circuit load 840a is reflected at the short circuit load 840a with a specific phase for the returned signal.

In test, the short circuit load 840a returns energy at a first phase and the open returns energy at a second phase. The short circuit load 840a places a voltage minimum at the short and full standing waves at every $\lambda/4$ and $3\lambda/4$ wavelengths on the transmission line proximal the short circuit load 840a. The open circuit 850a places full standing waves at the open and every $\lambda/2$ wavelengths on the transmission line proximal the open circuit 850a.

Using known open or short parameters and the present open and short parameters the phase angle and returned power of the antenna may be determined. An active tuning circuit may use one or more of these parameters to determine one or more system tuning parameters. For example, an active tuning circuit may be placed in the generator, the handle of the microwave energy delivery device or any other suitable location. Active tuning circuit may determine a range of mismatch and/or provide one or more calibration parameters to the system or may properly calibrate to the antenna feedpoint.

For example, the antenna and/or the tissue may be behaving inductively (i.e., $50\Omega+20\ \Omega j$ wherein the positive $20\ \Omega j$ is inductive) or capacitively (i.e., $50\Omega-20\ \Omega j$ wherein the negative $20\ \Omega j$ is inductive). Calibrating to the antenna feedpoint the system can identify if the antenna and/or tissue is behaving inductively or capacitively. As such, the system can incorporate a matching network to offset the impedance mismatch.

In yet another embodiment of the present disclosure calibration is performed by placing the antenna 940 of a microwave energy delivery device 915 in a calibration apparatus 900. Calibration apparatus 900 includes a chamber 910a configured to produce a known reflection and phase shift in an antenna 940a when the antenna 940a is placed adjacent the chamber 910a. Calibration is performed by placing the antenna 940a in a fixed position relative to the chamber 910a and driving the antenna 940a with a predetermined signal. The microwave generator 905a connects to microwave energy delivery device 920a via a cable 920a and measures one or more parameters indicative of the performance of the antenna 940a and compares the measured parameters with one or more predetermined parameters. The microwave generator 905a then determines one or more calibration parameters or one or more tuning parameters for the antenna 940a under test.

Figure 9A:
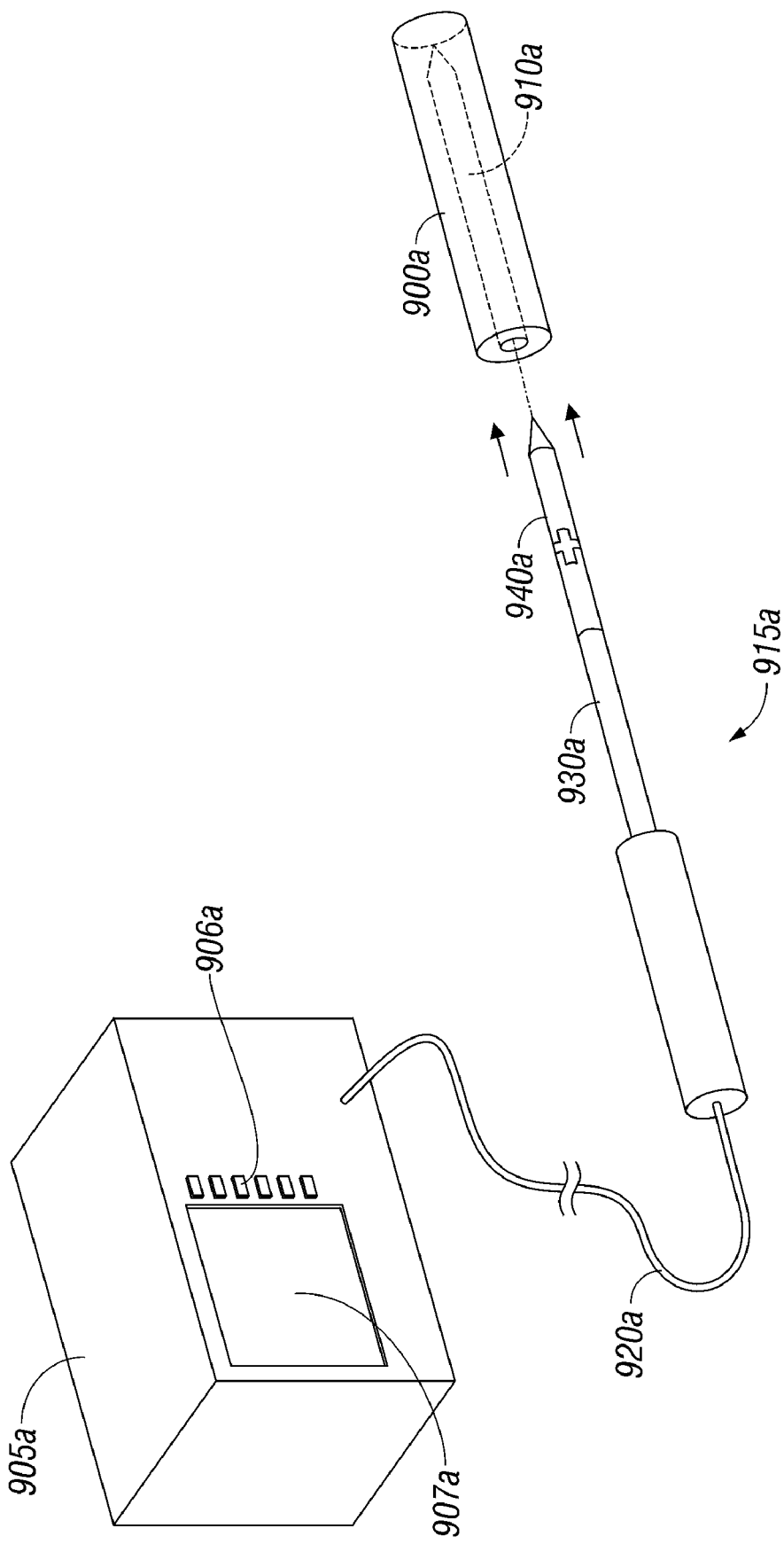
FIG. 9A is a schematic representation of a stand-alone calibration device for use in calibrating the microwave energy delivery, measurement and control system of the present disclosure.
Figure 9B:
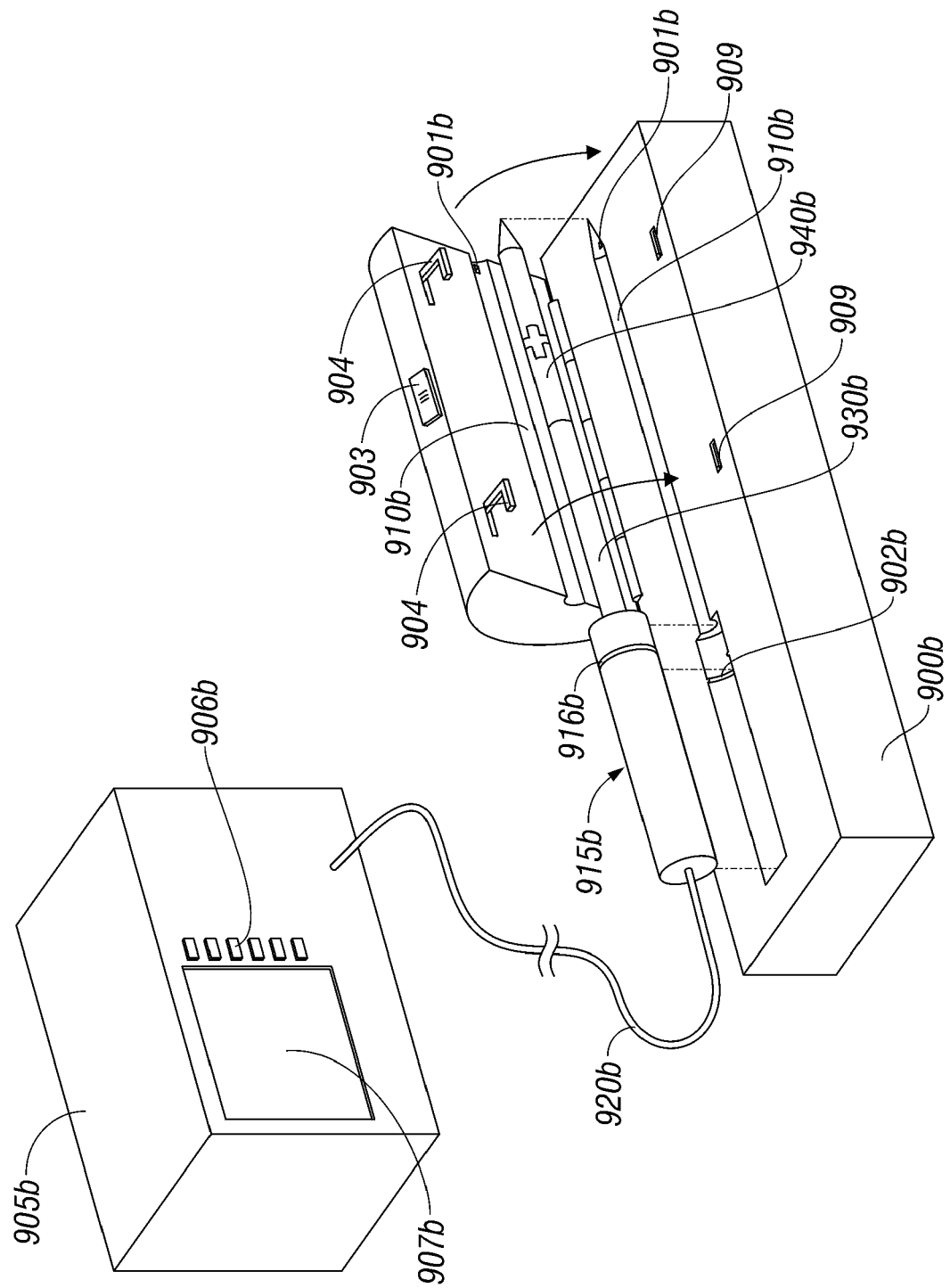
FIG. 9B is a schematic representation of a interfacing calibration device for use in calibrating the microwave energy delivery, management and control system of the present disclosure.

Chamber 910a may be a cylindrical shaped chamber configured to receive the antenna 940a. Chamber 910a may receive the distal end of the microwave energy delivery device 915a, including the antenna 940a, as illustrated in FIG. 9A, or chamber 940b may be configured to receive the microwave energy delivery device 915b, as illustrated in FIG. 9B. A positioning mechanism or stop mechanism may provide consistent placement of the antenna in the chamber. Stopping mechanism may include a sensing mechanism to sense the placement in the chamber. Sensing mechanism may provide a signal to the system to indicate that the antenna is in position. System, after receiving the signal from the sensing mechanism, may be configured to switch to a test mode in which the system drives the antenna with a predetermined microwave signal.

Calibration device 940a may be configured as a stand-alone device as illustrated in FIG. 9A, configured to interface with the microwave energy delivery device (not shown), configured to interface with the microwave generator, as illustrated in FIG. 9B or any combination thereof. Calibration device 900a may be a passive device that provides a load on the antenna 940a wherein the antenna response 940a to the load 900a (the calibration device) is known to the microwave generator 905a.

With reference to FIGS. 9A-9B, calibration device 900a, 900b may include a chamber 910a, 910b configured to receive at least a portion of the microwave energy delivery device 915a, 915b. Chamber 910a, 910b may be configured to receive the antenna 940a, 940b or the antenna and a portion of the device transmission line 930a, 930b. Chamber 910a, 910b is configured to position a microwave energy absorbing load relative to the antenna 940a, 940b.

In use, a clinician mates together the calibration device 900a, 900b and the microwave energy delivery device 915a, 915b, respectively. The antenna 940a, 940b of the microwave energy delivery device 915a, 915b is positioned relative to calibration device 900a, 900b, respectively, and a calibration procedure is performed. The calibration procedure may be initiated manually, by the clinician, via a microwave generator input 906a, 906b or interface screen 907a, 907b or by an input on the microwave energy delivery device (not shown). Alternatively, the calibration procedure may be automatically initiated by the microwave generator 905b. For example, placement of the antenna 940b relative to the load in the calibration device 900b may trigger a sensor 901b or input to the microwave generator 905b (not shown) and a calibration procedure may be automatically initiated.

In one embodiment, the calibration procedure includes the steps of driving the antenna with a microwave energy signal, measuring at least one parameter related to the antenna and generating at least one antenna calibration parameter. The microwave energy signal may be a predetermined signal, a signal selected by the clinician or a signal selected for the specific antenna. The one or more parameters related to the antenna may include one of forward power, reflected power, impedance and temperature. The at least one antenna calibration parameter is related to the operation of the antenna, such as, for example, a parameter related to antenna tuning, a parameter related to the resonance of the antenna, a parameter related to antenna construction or any other suitable parameter related to microwave energy delivery.

Calibration device may be configured to interface with one of the microwave energy delivery device or the microwave generator. As illustrated in FIG. 9B, calibration device 900b may connect to the microwave generator 905b via a cable 920b. In another embodiment, the calibration device 900b may include a connector (not shown) that interfaces with the microwave energy delivery device 915b when mated together. Connection between the calibration device 900b and microwave generator 905b or microwave energy delivery device 915b may also be configured as a wireless connection. Connection may include one or more digital or analog connections or may include a suitable communication means, such as, for example, TCP/IP, OSI, FTP, UPnP, iSCSI, IEEE 802.15.1 (Bluetooth) or Wireless USB. Calibration device 900b may provide one or more parameters related to the calibration device 900b and/or the calibration procedure to one of the microwave energy delivery device 915b and the microwave generator 905b.

Calibration device 900b may further include a positioner 902b to position the microwave energy delivery device 915b in one or more positions relative to the calibration device 900b. As illustrated in FIG. 9B, positioner 902b aligns with notch 916b on the microwave energy delivery device 915b such that the calibration device 900b and microwave energy delivery device 915b mate in position. Positioner 902b and notch 916b are configured to position the antenna 940b in a desirable position relative to chamber 910b. Positioner may be any suitable means of positioning the microwave energy delivery device 915b relative to the calibration device 900b such as, for example, a latch, a catch, a locking clam-shell, a clip, a locking or positioning pin, an unique shaped appendage and matching recessed portion configured to receive the appendage and any other suitable positioning device.

Calibration device 900b may further include a locking mechanism 903, 904, 909 for locking the calibration device 900b to the microwave energy delivery device 915b. As illustrated in FIG. 9B, catches 904 align with slots 909 when chamber 910b is in a closed position. Slide 903 actuates catches 904 within the slots thereby locking the chamber in a closed position. Any suitable locking mechanism may be used such as, for example, a clip, a latch, a pressed fit pin, a locking or self-closing hinge, a magnetic or electronic closure mechanism or any other suitable locking mechanism. Slide 903 or other locking release mechanism may be configured to be disabled when the antenna 940b is activated thereby preventing the calibration device 900b from releasing the microwave energy delivery device 915b during calibration or energy delivery.

As various changes could be made in the above constructions without departing from the scope of the disclosure, it is intended that all matter contained in the above description shall be interpreted as illustrative and not in a limiting sense. It will be seen that several objects of the disclosure are achieved and other advantageous results attained, as defined by the scope of the following claims.

What is claimed is:

1. A system for calibrating a microwave energy delivery device, comprising:
   a body defining a chamber portion therein, the body including:
      a first body portion configured to receive and position a microwave energy delivery device; and
      a second body portion configured to engage the first body portion and form the chamber portion therebetween, wherein the first body portion and the second body portion are hingedly engaged about a fixed axis of rotation,
   wherein the chamber portion at least partially surrounds a microwave antenna on the microwave energy delivery device and is configured to receive at least a portion of the microwave energy delivery device and the body is configured to absorb energy transmitted by the microwave antenna of the microwave energy delivery device at a predetermined absorption rate.

2. The system of claim 1, wherein the chamber portion formed by the body is an elongate cylindrical chamber, the elongate cylindrical chamber adapted to receive the microwave antenna of the microwave energy delivery device.

3. The system of claim 1, wherein the chamber portion is configured to engage the microwave antenna of the microwave energy delivery device within the chamber portion.

4. The system of claim 1, wherein the first and second body portions further include a locking mechanism that locks the first body portion to the second body portion.

5. The system of claim 4, wherein the locking mechanism is selected from one of a clip, a latch, a pin, a locking hinge, a self closing hinge, a magnetic lock and an electronic closure mechanism.

6. The system of claim 1, wherein the body further includes a positioner to position the microwave energy delivery device in a fixed position relative to the chamber portion.

7. The system of claim 6, wherein the positioner on the body corresponds to a substantially similar interface on the microwave energy device, wherein the positioner and the interface mate with each other to position the microwave energy delivery device in a fixed position relative to the chamber portion.

8. The system of claim 7, wherein the positioner is a recessed portion of the body and the interface is a raised portion of the microwave energy delivery device, wherein the recessed portion and the raised portion mate together and position the microwave energy delivery device.

9. The system of claim 1, wherein the first body portion and the second body portion surround at least a portion of the microwave energy delivery device in a first condition and are spaced relative to a portion of the microwave energy delivery device in a second condition.

10. A system for calibrating a microwave energy delivery device comprising:
 a microwave energy delivery device;
 a microwave generator configured to deliver a microwave energy signal to the microwave energy delivery device; and
 a microwave system calibration apparatus including:
  a body defining a chamber portion therein, the chamber portion being configured to receive at least a portion of the microwave energy delivery device, the body being configured to absorb microwave energy, transmitted by the microwave energy delivery device, at a predetermined absorption rate, the body further including:
   a first body portion configured to receive and position the microwave energy delivery device; and
   a second body portion configured to engage the first body portion and form the chamber portion therebetween, the chamber portion at least partially surrounds a microwave antenna on the microwave energy delivery device,
   wherein the first body portion and second body portion are hingedly engaged about a fixed axis of rotation;
  wherein the microwave generator is configured to measure at least one measured parameter related to the microwave energy signal delivered to the microwave energy delivery device and to determine at least one calibration parameter related to the calibration of the microwave energy delivery device.

11. The system of claim 10, wherein the chamber portion formed by the body is an elongate cylindrical chamber, the elongate cylindrical chamber being adapted to receive the microwave antenna of the microwave energy delivery device.

12. The system of claim 10, wherein the at least one measured parameter is selected from a group consisting of forward power, reflected power and temperature.

13. The system of claim 10, wherein the at least one calibration parameter is selected from a group consisting of phase, frequency and impedance.

14. The system of claim 10, wherein the microwave generator is configured to determine engagement of the microwave energy delivery device with the microwave system calibration apparatus.

* * * * *